(12) United States Patent
Dasgupta et al.

(10) Patent No.: US 7,964,411 B2
(45) Date of Patent: Jun. 21, 2011

(54) MEMBRANE BASED CONCENTRATORS

(75) Inventors: Purnendu Dasgupta, Arlington, TX (US); Masaki Takeuchi, Tokushima (JP); Kannan Srinivasan, Tracy, CA (US)

(73) Assignees: Dionex Corporation, Sunnyvale, CA (US); Board of Regents, The University of Texas, Austin, TX (US)

( * ) Notice: Subject to any disclaimer, the term of this patent is extended or adjusted under 35 U.S.C. 154(b) by 1016 days.

(21) Appl. No.: 11/762,000

(22) Filed: Jun. 12, 2007

(65) Prior Publication Data

US 2008/0311672 A1     Dec. 18, 2008

(51) Int. Cl.
*G01N 30/02* (2006.01)

(52) U.S. Cl. ......... 436/161; 436/178; 436/535; 422/70; 422/89; 422/527; 422/528; 422/530; 210/159; 210/167.07; 210/180; 210/181; 210/198.2; 210/635; 210/638; 210/640; 210/645; 210/650; 210/651; 210/656; 210/660; 210/669; 210/670; 73/19.02; 73/23.35; 73/61.43

(58) Field of Classification Search ............... 422/70, 422/89, 101, 527, 528, 529, 530; 436/161, 436/178, 535; 210/180, 645, 656, 659, 159, 210/167.07, 181, 198.2, 635, 638, 640, 649, 210/650, 651, 660, 669, 670; 73/19.02, 23.35, 73/61.43
See application file for complete search history.

(56) References Cited

U.S. PATENT DOCUMENTS

| 3,970,534 | A | | 7/1976 | Fujiwara et al. |
|---|---|---|---|---|
| 4,055,987 | A | | 11/1977 | McFadden |
| 4,407,846 | A | | 10/1983 | Machi et al. |
| 4,414,090 | A | | 11/1983 | D'Agostino et al. |
| 4,465,554 | A | | 8/1984 | Glass |
| 4,474,664 | A | | 10/1984 | Stevens et al. |
| 4,604,363 | A | | 8/1986 | Newhouse et al. |
| 4,751,004 | A | | 6/1988 | Stevens et al. |
| 4,867,947 | A | | 9/1989 | Andresen et al. |
| 4,999,098 | A | | 3/1991 | Pohl et al. |
| 5,039,420 | A | * | 8/1991 | Klein et al. .............. 210/645 |
| 5,100,623 | A | | 3/1992 | Friswell |
| 5,352,360 | A | | 10/1994 | Stillian et al. |
| 5,567,307 | A | * | 10/1996 | Karmarkar ........... 210/198.2 |
| 5,569,365 | A | | 10/1996 | Rabin et al. |
| 5,597,481 | A | * | 1/1997 | Stillian et al. ........... 210/198.2 |

(Continued)

OTHER PUBLICATIONS

Cappiello, A et al. Liquid chromatography-electron ionization mass spectrometry: fields of application and evaluation of the performance of a direct-ei interface. *Mass Spectrom. Rev.* 24:978-989 (2005).

(Continued)

*Primary Examiner* — In Suk Bullock
*Assistant Examiner* — Dennis M White
(74) *Attorney, Agent, or Firm* — Morgan, Lewis & Bockius LLP; David J. Brezner

(57) ABSTRACT

A sample concentrator for concentrating analytes in a solvent-containing liquid sample stream, including concentrator housing having a sample stream flow channel and a gas stream flow channel having an inlet and an outlet, a heater for gas in the gas stream conduit, and a hydrophilic ion exchange or non-ionic membrane barrier separating said gas stream flow channel and said sample stream flow channel. Solvent is evaporated from the liquid sample stream in said sample stream flow channel in or at the interface with said membrane, when the gas stream is at an elevated temperature. A regeneration step is used to regenerate the ion exchange membrane barrier.

15 Claims, 22 Drawing Sheets

U.S. PATENT DOCUMENTS

| | | | |
|---|---|---|---|
| 5,597,734 | A | 1/1997 | Small et al. |
| 5,897,838 | A | 4/1999 | Kempe |
| 6,146,595 | A | 11/2000 | Mikulsky |
| 6,425,284 | B1 | 7/2002 | Srinivasan et al. |
| 6,610,546 | B1 | 8/2003 | Liu et al. |
| 6,620,620 | B1 | 9/2003 | Anderson et al. |
| 6,656,361 | B1 | 12/2003 | Herron et al. |
| 2004/0203175 | A1 | 10/2004 | Li et al. |
| 2006/0037911 | A1* | 2/2006 | Dasgupta et al. ............. 210/656 |
| 2006/0043023 | A1 | 3/2006 | Srinivasan et al. |
| 2006/0057733 | A1 | 3/2006 | Liu et al. |
| 2006/0062982 | A1 | 3/2006 | Hammond Cunningham et al. |
| 2007/0062873 | A1 | 3/2007 | Liu et al. |

OTHER PUBLICATIONS

Zwiener, C.; Frimmel, F. H. LC-MS analysis in the aquatic environment and in water treatment—a critical review. Part II: Applications for emerging contaminants and related pollutants, microorganisms and humic acids. *Anal. Bioanal. Chem.*378:851-861 (2004).

Megoulas, N. C.; Koupparis, M. A. Twenty years of evaporative light scattering detection. *Crit. Rev. Anal. Chem.* 35:301-316 (2005.

Gormley P. G.; Kennedy, M. Diffusion from a stream flowing through a cylindrical tube. *Proc. R.. Ir. Acad. Sci.* 52A:163-169 (1949).

Ullah, SM. R.; et al. Asymmetric membrane fiber-based carbon dioxide removal devices for ion chromatography. *Anal. Chem.* 76:7084-7093 (2004).

Dasgupta, P. K. Automated measurement of atmospheric trace gases. Diffusion-based collection and analysis. *ACS Adv. Chem. Ser.* 232:41-90 (1993).

Yeager, H. L. Transport properties of perfluorosulfonate polymer membranes. *ACS Symp. Ser.* 180:41-64 (1982).

Waiz, S.; Cedillo, B. M.; et al. Dispersion in open tubular reactors of various geometries. *Anal. Chim. Acta* 428:163-171 (2001).

Dasgupta, P. K. Linear and helical flow in a perfluorosulfonate membrane of annular geometry as a continuous cation exchanger. *Anal. Chem.*56:96-103 (1984).

Dasgupta, P. K. Annular helical suppressor for ion chromatography. *Anal. Chem.* 56:103-105 (1984).

Boring, C. B.; Al-Horr, R.; et al. Field measurement of acid gases and soluble anions in atmospheric particulate matter using a parallel plate wet denuder and an alternating filter-based automated analysis system. *Anal. Chem.* 74(6):1256-1268 (2002).

Bishop, EJ and S Mitra. On-line membrane preconcentration for continuous monitoring of trace pharmaceuticals, *Journal of Pharmaceutical and Biomedical Analysis*, 37:81-86 (2005).

Guo X and S Mitra. On-line membrane extraction liquid chromatography for monitoring semi-volatile organics in aqueous matrices, *J Chromatog. A* 904:189-196 (2000).

Bishop, EJ and S Mitra. Hollow fiber membrane concentratore for on-line preconcentration. *J Chromatogr. A* 1046:11-17 (2004).

Encyclopedia of Polymer Science and Engineering, Supplement vol. 2.sup.nd edition, John Wiley & Sons 678 (1989).

Yamakawa, S. Surface modification of fluorocarbon polymers by radiation-induced grafting for adhesive bonding. *Macromolecules* 12(6):1222-1227 (1979).

Yamakawa, S et al. Surface modification of polyethylene by radiation-induced grafting for adhesive bonding. 2. Relationship between adhesive bond strength and surface structure. *Macromolecules* 9(5):754-758 (1976).

Fritz, James S., Gjerde, Douglas T., "Ion Chromatography" Wiley-VCH Verlag GMBH, pp. 191-200 (2000).

* cited by examiner

Figure 3A — Top view (cross-section)

Figure 3B — Side view (cross-section)

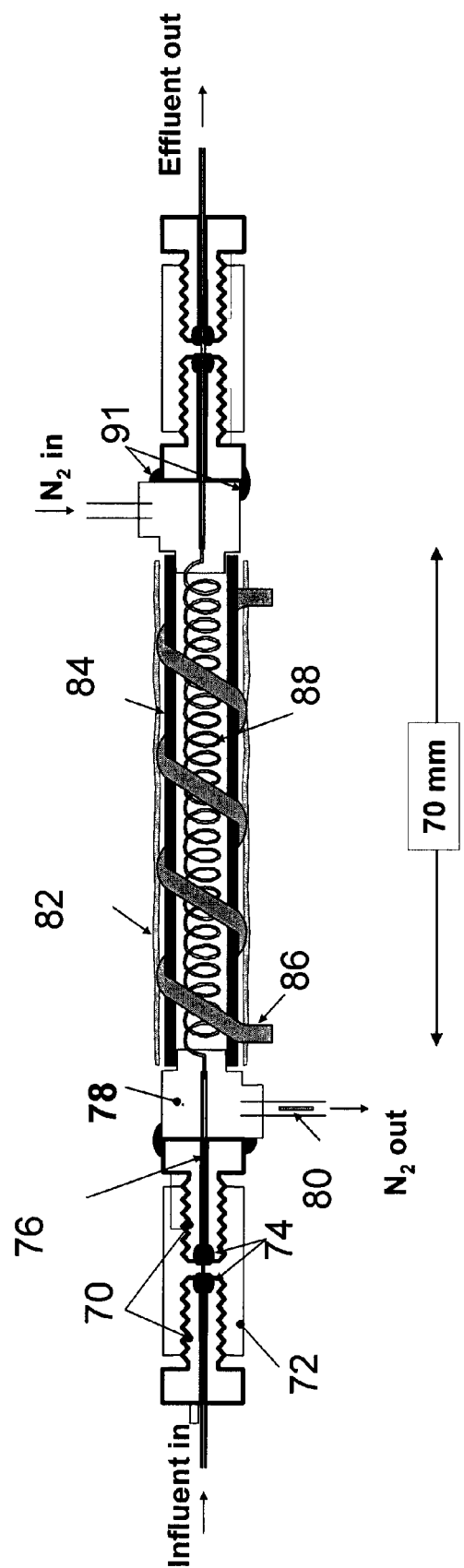
Figure 5A
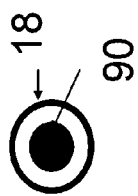
Figure 5B Cross-section of membrane 88

MEMBRANE BASED CONCENTRATORS

BACKGROUND OF THE INVENTION

1. Field of Invention

The present invention relates to a sample concentrator system. More particularly, the present invention relates to an online sample concentrator system based on solvent evaporation for use in a chromatography system.

2. Description of the Related Art

Preconcentration in a chromatography system, performed prior to detection of the analytes, typically is performed by concentrating the analytes in a column that is preferably selective to the analytes of interest and then subsequently eluting the trapped or concentrated species for further analysis. When analyte concentrations are too low to produce an adequate detector response a variety of solutions are implemented. Traditional solutions to this problem include prior sample workup to increase analyte concentration, large volume injection with or without preconcentration on a solid phase, adoption of a more sensitive detector, or a change to a more sensitive detection approach that may involve either pre- or post-column derivatization. Preconcentration methods using a solid phase are more prevalent in ion chromatography. For example when pursuing trace level analysis of anions in ultra pure water (UPW) samples, preconcentration is typically used to concentrate the anions onto a concentrator column. In addition to anions, the approach also concentrates the dissolved carbon dioxide which manifests as carbonate during analysis. Depending on the concentration, the presence of the carbonate peak may interfere with quantitation of other anions such as sulfate. For UPW samples it would be useful to have a method that only concentrates the anions without the dissolved carbon dioxide. When pursuing trace analysis with environmental samples such as drinking water the detection of trace ions in the presence of matrix ions is an issue. Concentrating the trace ions also typically concentrates the matrix ions. It would be useful to have a selective concentration mechanism.

Other means of improving sensitivity is presently pursued by preferentially eliminating the solvent using solvent condensation or evaporation techniques. Nitrogen or inert gas assisted evaporation, distillation, rotary evaporation, evaporation with tube heaters, lypholization and the like are different approaches used in preferentially removing the solvent. These are all typically offline methods that are implemented using bench top equipment and as such are not amenable for use with chromatographic equipment or inline chromatography.

In liquid chromatography there are at least two detection approaches that incorporate the concept of solvent removal before detection. One involves the interface between liquid chromatography and mass spectrometry (LC-MS [1, 2]). Another application area is in evaporative light scattering detection (ELSD,[3]). In both of these approaches, the detector is mass-sensitive, rather than concentration sensitive and detection is accomplished in the gas phase. Additionally the rationale for removing the solvent was to improve compatibility with the detector. For example the interfaces such as thermospray, electrospray, atmospheric pressure chemical ionization and ionspray were all designed to reduce the solvent being transmitted to the mass spectrometer. The above detectors are all mass sensitive detectors.

In recent years, technological developments have permitted commercialization of capillary and intermediate scale chromatographic equipment. These new generations of low cell-volume concentration sensitive detectors that for example measure optical absorbance, electrical conductance or fluorescence display the same (or even better) concentration limits of detection (LODs) compared to their older larger cell volume counterparts. Nevertheless, the majority of liquid chromatography practice still centers on standard bore (4.0-4.6 mm i.d.) columns with a typical eluent flow rate of the order of 1 mL/min. In the vast majority of cases, if the column effluent from such a system is split and only 10% of the original flow is sent to a low cell-volume detector, there will be no apparent deterioration of sensitivity compared to the entire effluent going through a standard, larger cell volume detector. It would useful if the sensitivity when operating with concentration sensitive detectors can be improved.

The patent literature includes systems that use a batch mode of operation for concentrating the analyte stream. These approaches do not preserve the separation and involve multiple steps and transfer processes that can potentially hinder the recovery and quantitation of analytes of interest.

For example, U.S. Pat. No. 4,055,987 describes an interface between a liquid chromatograph and a mass spectrometer. The interface comprised of a thin ribbon which received the effluent from the liquid chromatography column and the ribbon is passed into several vacuum locks to remove the residual solvent. The residual solute is flash vaporized into the ionization chamber of the mass spectrometer.

U.S. Pat. No. 4,465,554 describes an apparatus for evaporating liquid fractions by directing a hot steam of non reacting gas directly on the surface of the sample fraction collected to aid evaporation. This approach is an offline approach and by collecting the fractions, the separation is not preserved.

U.S. Pat. No. 4,604,363 describes an automatic evaporator system performing evaporation and concentration coupled with solvent exchange. The samples are delivered to a temperature and pressure controlled evaporation chamber. This again is a batch mode device.

U.S. Pat. No. 4,867,947 describes a moving belt interface that strips away the eluent continuously while leaving behind a residue for analysis by a mass spectrometer. A probe tip was also disclosed that sampled the residue by direct ionization. The peak shapes are not preserved, and this method is not well suited for post analytical steps.

U.S. Pat. No. 5,897,838 describes an apparatus for concentration or evaporation of aqueous solutions. The approach involved a combination of vacuum and directing an air stream on the sample that is residing in a vial in a multiplate well.

U.S. Pat. No. 5,100,623 describes a temperature controlled water bath for the function of evaporation. The apparatus also incorporated means of adding solvents to reconstitute the sample.

U.S. Pat. No. 6,146,595 describes a closed positive evaporation system for evaporating samples prior to analysis. This approach is not continuous.

U.S. Pat. No. 6,620,620 describes batch mode apparatus that facilitated controlled evaporation of a liquid. The apparatus includes a deposition surface plate on which the sample to be analyzed is deposited in a drop by drop fashion.

U.S. Pat. No. 6,656,361 discloses a membrane assisted evaporation process to dry brine solutions. The purpose of this work was to replace drilled oil from salt caverns with salt rather than diluted salt solution. Therefore there was a need to concentrate or evaporate the water from the brine solution.

U.S. application 20040203175 describes an apparatus for concentrating one or more analytes in a flowing liquid stream. The solvent components are evaporated by flowing the sample stream through a transfer tube that is heated and evaporation was accomplished on hanging droplets of the flowing samples. Partial evaporation is accomplished by operating at a temperature below the boiling point of the solvent. The drops are accumulated in a collection device that is also heated to effect further evaporation.

Bishop and Mitra (J. Chromatogr. A 1046 (2004) 11-17 and J. Pharmaceutical and Biomedical Analysis 37, 2005, 81-86) describes an inline preconcentration method by evaporating the solvent from a sample stream in a membrane based evaporator module prior to injection onto a HPLC system for analysis. The hollow fiber based evaporator module was fitted with five strands of hollow fiber membranes comprising of polypropylene substrate that was coated with siloxane. Another device used a commercially available Nafion® membrane from Perma pure, Toms River, N.J. USA) and designed for gas phase drying applications. The second reference cited above describes the use of the Nafion® membrane-based module. A heat tape was used to heat the hollow fiber module. In the first cited publication the sample after evaporation was collected into a sample vial for further analysis. The above method was a pre injection sample pretreatment approach and suffered from the limitation of coping with possible contamination issues from the sample vials. The second publication describes a direct interface to the injection valve. The sample was delivered to the hollow fiber module using a pump. Both devices allowed evaporation of solvent from the sample stream thereby concentrating the sample stream.

In suppressed ion chromatography there is a need for a non chromatographic concentration method. Additionally, there is a need for a concentration apparatus that would enhance the sensitivity without significantly affecting chromatographic separation. Additionally in multidimensional separation schemes it would be useful to have an inline approach thereby avoiding any sample transfer related loss. It would also be useful to have a method that would concentrate analytes selectively.

SUMMARY OF THE INVENTION

In one embodiment, the present invention is directed to a sample concentrator for concentrating analytes in a solvent-containing liquid sample stream. The concentrator comprises (a) a concentrator housing having a sample stream flow channel and a gas stream flow channel having an inlet and an outlet, (b) a gas source, (c) a gas stream conduit providing continuous or discontinuous fluid communication between said gas source and said gas stream flow channel inlet, (d) a heater operatively associated with said gas source, gas stream conduit or gas stream flow channel, (e) a hydrophilic membrane barrier separating said gas stream flow channel and said sample stream flow channel, said membrane barrier preventing bulk liquid flow but permitting the flow of solvent evaporated from said liquid sample stream in said sample stream flow channel in or at the interface with said membrane, when said gas stream is at an elevated temperature, and (f) a source of a regenerant liquid in continuous or discontinuous fluid communication with said gas stream flow channel or said sample stream flow channel.

Another embodiment is a method of concentrating the analytes after they have been chromatographically separated. The method comprises (a) flowing the liquid sample stream at a first temperature through a sample stream flow channel in a sample concentrator separated from a gas stream flow channel by a hydrophilic membrane barrier having ion exchange sites, (b) concentrating the analytes by flowing a gas stream through said gas stream flow channel at a second temperature at least about 10° C. higher than the temperature of said liquid sample stream, to elevate the temperature of the liquid sample stream to cause a portion of the solvent in or at the interface with said membrane barrier to evaporate and flow through the membrane to be carried away in the flowing gas stream in said gas stream flow channel, and (c) regenerating said ion exchange sites.

In other embodiments, the present invention is directed to sample concentrators of a similar type but which do not necessarily regenerate the membrane or use a source of regenerant solution.

In one embodiment the concentrator is disposed downstream of a chromatographic separator for the sample analytes.

In another embodiment, the invention is directed to a method of concentrating analytes in a solvent-containing liquid sample stream.

In a further embodiment, concentration is performed using a non-ionic hydrophilic membrane which does not require regeneration.

In another embodiment, prior to concentration, the liquid sample stream flows through a suppressor to remove ions of opposite charge to the analyte ions.

DESCRIPTION OF THE DRAWINGS

FIGS. 3A-3C illustrate a maze-type concentrator.

FIGS. 5A and 5B illustrate a helix concentrator.

DETAILED DESCRIPTION OF THE PREFERRED EMBODIMENTS

Figure 1:
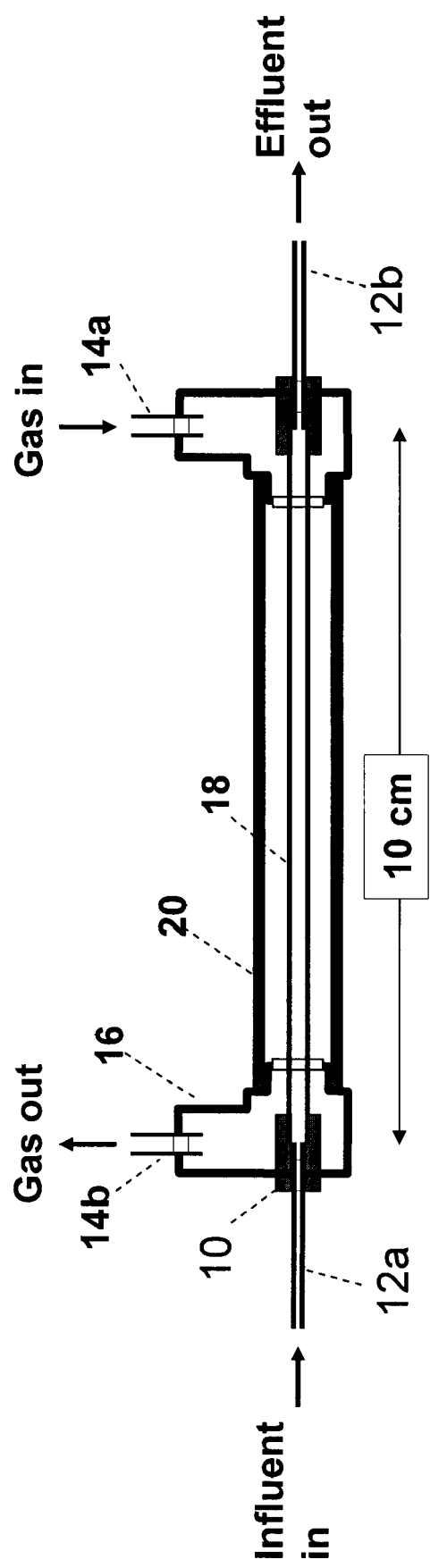
FIG. 1 illustrates a membrane tube-based concentrator according to the invention.

In one aspect, the present invention is directed to a sample concentrator for concentrating analytes in a solvent-containing liquid sample stream. The concentrator comprises (a) a concentrator housing having a sample stream flow channel and a gas stream flow channel having an inlet and an outlet, (b) a gas source, (c) a gas stream conduit providing continuous or discontinuous fluid communication between said gas source and said gas stream flow channel inlet, (d) a heater operatively associated with said gas source, gas stream conduit or gas stream flow channel, (e) a hydrophilic membrane barrier separating said gas stream flow channel and said sample stream flow channel, said membrane barrier preventing bulk liquid flow but permitting the flow of solvent evaporated from said liquid sample stream in said sample stream flow channel in or at the interface with said membrane, when said gas stream is at an elevated temperature, and (f) a source of a regenerant liquid in continuous or discontinuous fluid communication with said gas stream flow channel or said sample stream flow channel.

In another aspect, the invention is directed to a method of concentrating analytes in a solvent-containing liquid sample stream. The method comprises (a) flowing the liquid sample stream at a first temperature through a sample stream flow channel in a sample concentrator separated from a gas stream flow channel by a hydrophilic membrane barrier, and (b) concentrating the analytes by flowing a gas stream through said gas stream flow channel at a second temperature at least about 10° C. higher than the temperature of said liquid sample stream, to elevate the temperature of the liquid sample stream to cause a portion of the solvent in or at the interface with said membrane barrier to evaporate and flow through the membrane to be carried away in the flowing gas stream in said gas stream flow channel which preferably is performed using such apparatus In a specific aspect of the present invention, the concentrator hydrophilic membrane barrier, termed herein a "solvent removal membrane," a "membrane barrier" or a "membrane", facilitates the removal of an aqueous solvent while maintaining the peak shapes with minimal loss of peak efficiency. In one embodiment, the membrane is polymer-based with hydrophilic moieties. Such moieties include any ones that render the membrane hydrophilic as that term is commonly used. Typically, a hydrophilic membrane is characterized by hydrogen bonding groups.

In one embodiment, the membrane includes ion exchange sites classified as an ion exchange membrane. Any ion exchange membrane could be used as per the present invention since they carry functionalities that render them hydrophilic. Preferred ion exchange hydrophilic moieties include sulfate, sulfonate, carboxylate, phosphate, (quaternary) ammonium and hydroxide groups and combinations thereof. One such membrane can be a symmetric membrane such as Nafion® comprising of a hydrophilic groups that are scattered throughout the membrane or can have an asymmetric core comprising of polypropylene or polyethylene with a thin layer of hydrophilic coating on top such as Nafion coated on top of a porous polypropylene layer. The coating is preferably pin-hole free thereby making the membrane impermeable to bulk liquid flow. The membrane can be grafted with hydrophilic groups for example by taking polyethylene tubing and irradiating this tubing in the presence of monomers with gamma or ionizing radiation as described in U.S. Pat. Nos. 3,970,534, 4,414,090, 4,407,846, 4,999,098 and 5,352,360. Functionalization of the polymer clad membrane can occur by methods that are well known such as by reacting a polystyrene clad membrane with sulfuric acid to create sulfonic acid groups on the surface of the membrane. The presence of the sulfonic acid groups renders the membrane hydrophilic. It is preferable to regenerate such ion exchange membranes continuously (during a chromatographic separation), or discontinuously in a batch mode so that regeneration does not occur at the same time as separation and detection.

Similarly a radiation grafted polyvinyl acetate membrane on polyethylene substrate could be hydrolyzed to yield a hydrophilic hydroxide containing membrane. Techniques suitable for the modification of the membrane polymer surface by graft polymerization of a monomer of monomers from active sites generated on solid polymer surfaces are well known (See, e.g., Encyclopedia of Polymer Science and Engineering, Supplement Vol, 2.sup.nd edition, John Wiley & Sons (1989) 678, Macromolecules, Vol. 9, (1976), 754, and Macromolecules, Vol. 12, (1979), 1222). The most common technique is gamma radiation using radiation sources such as a $^{60}CO$ source, which generates surface radicals, but thermal, photochemical, plasma, and wet chemical methods can also be used to introduce free radical sites for initiation. Monomers can be present in the gas phase, in solution, or as neat liquids. Preferred graft level as measured by a weight gain of the membrane after the radical polymerization step are in the 10-50% regime and more preferably in the 15-25% regime. The surface graft polymerization techniques can be used to modify the ion exchange membrane to include weakly acidic function groups on the outer wall of the membrane.

Also, non-ionic hydrophilic membranes, i.e. ones without ion exchange sites, may be used. Such non-ionic functional groups include non-ion exchange hydrophilic groups such has hydroxyl, diols, esters, amides, phenol and the like. Membranes could also be prepared from mixtures of polyvinylidene fluoride and polyvinyl acetate. A hydrolysis step converts the acetate groups to hydroxyl groups. Non ionic hydrophilic membranes can be prepared as discussed previously by radiation grafting with non ionic monomers such as an epoxide containing monomer for example, methylglycidyl methacrylate, methyl glycidyl acrylate, allyl glycidyl ether, allylphenol glycidyl ether and glycidyl methacrylate. Other suitable neutral monofunctional monomers which can be polymerized to form non-ionic hydrophilic membranes include hydroxy- and alkoxyalkyl acrylates, such as, for example, 2-hydroxyethyl acrylate, 2-hydroxyethyl methacrylate, hydroxypropyl acrylate, hydroxypropyl methacrylate, 2-methoxyethyl acrylate, 2-phenoxyethyl acrylate, 2-phenoxyethyl methacrylate, and ethers such as glycidyl ethers such as 1.4 Butanediol diglycidyl ether, allyl glycidyl ether, and combinations thereof.

The term "hydrophilic" excludes totally hydrophobic membranes such as organic polymers which do not include hydrophilic moieties for example polypropylene or polyethylene tubing when used as is or with hydrophobic coatings. For ion exchange membranes, it is preferable that the exchangeable ions be predominantly in the regenerated form as that term is used in suppressors used in ion chromatography. For example, anion exchange membranes with amine groups are preferably present predominantly in the exchangeable hydroxide ion (regenerated) form and cation exchange membranes with sulfonic acid groups are preferably present predominantly in the exchangeable hydronium ion (regenerated) form during concentration.

As set forth above, when using ion exchange membranes, it is preferable to regenerate the ion exchange membranes. Regeneration can be accomplished by flowing an acid or base solution past or through the membrane. The regeneration could be accomplished by well known methods of the prior art as described in U.S. Pat. Nos. 4,474,664; 4,999,098; 5,569,365; 5,597,734; 6,610,546; US 2006/0057733 and included references therewithin.

In general, regeneration may be performed chemically and/or electrolytically. Chemical regeneration can be accomplished by flowing a regenerant solution, such as an acid for a cation exchange membrane or a base for an anion exchange membrane with cation exchange groups. As used herein, the regenerant solution includes any solution which is conventionally used for regeneration of a suppressor in ion chromatography. In one embodiment, the regenerant solution flows from a source through the gas flow channel simultaneously with the gas during a chromatographic separation run. (This is termed a continuous run.) The gas and regenerant may be intimately mixed prior to or during flow through the channel, such as in the form of an aerosol-like flowing fluid. A typical experimental setup for pursuing this is described in U.S. Pat. No. 6,425,284. A sufficient amount of liquid should be used to accomplish regeneration. Suitably, the regenerant concentration is in the 10 mM to 2000 mM regime and more preferably in the 10 to 100 mM regime. Preferable flow rate of the regenerant is in the 0.2 ml/min to 10 ml/min and more preferably in the 0.5 to 2 ml/min regime. A sufficient flow rate of gas should be used to carry away the evaporated solvent and the consumed regenerant.

In another embodiment, the regenerant solution flows through the sample stream flow channel. This is accomplished in a batch or discontinuous mode. That is, valving can be used to terminate the flow of sample solution through the sample stream flow channel and then to flow the regenerant solution therethrough. Suitably, this valving could utilize an autosampler as set forth in the examples. On completion, a wash solution preferably is passed through the channel to remove the acid or base which could interfere with the analysis.

In another embodiment, regeneration may be performed electrolytically as described, e.g. in U.S. Pat. No. 5,352,360. This can be done on a continuous basis during a chromatographic run. In this case, an acid or base regenerant solution or a wash stream can be pumped through the gas stream flow channel while applying an electric charge across the membrane through electrodes in electrical communication with the gas stream flow channel and sample stream flow channel, respectively, to electrolyze water at the anode and cathode as illustrated in the '360 patent. Sufficient water flows through the gas stream flow channel for this purpose.

In a specific embodiment, anion exchange membranes may be regenerated to the hydroxide form by pumping alkali hydroxide reagents such as sodium hydroxide, potassium hydroxide, tetramethylammonium hydroxide and the like. Typical regenerant concentration would be in the 10 mN to 2 N regime, more typically 25 mN to 100 mN regime. It is also possible to regenerate the membrane using a gas assisted approach as disclosed in U.S. Pat. No. 6,425,284. This approach uses a combination of an inert gas and regenerant. Another approach would be to regenerate the membrane by electrolytically supplying hydroxide ions as disclosed in U.S. Pat. No. 4,999,098. Combinations of the above discussed methods could also be used for example supply regenerant that consisted of both chemically supplied and electrolytically generated regenerant ions. Many possibilities exists. The regeneration would be preferably done in a batch mode on run to run basis, or on every few runs basis. It is also possible to operate in a continuously regenerated mode in conjunction with gas flow. The regenerant counter ions could be preferably bulky such as tetra butyl ammonium ion in order to minimize counter ion leakage into the sample stream. A DI water rinse could be pursued after the regeneration step. Regenerants could be recycled as described in 2007/0062873 and included references there within.

In one embodiment, the membrane is symmetric in that it includes hydrophilic groups throughout its cross-section. Suitable membranes of this type include ion exchange membranes such as one sold under the Nafion® name.

Other membranes are coated with a layer including hydrophilic groups which cause the membrane to have hydrophilic characteristics. Suitable membranes of this type can include porous hyrophobic or hydrophilic structural membranes with a hydrophilic coating of Nafion. Preferably the coating is present on both sides of the membrane. The hydrophilic functionality as per the present invention allows aqueous volatile components to permeate across the membrane.

The membrane is preferably in a tubular or hollow fiber format such as in the form of a capillary. A preferred inner diameter of the tubular membrane is 1 to 1000 microns, more preferably 50 to 500 microns. The membrane could also be a flat or sheet-like configuration separating two flow channels.

The tubular membrane may be filled with a rod, filament or other suitable filler which serve to reduce the diffusion distance to the membrane wall, to promote mixing, and to reduce the delay volume as described in U.S. Pat. No. 4,751,004. Preferred materials for the filler are polyethylene or polypropylene or nylon or other suitable polymer-based materials such as ion exchange resins and the like. Ion exchange fibers could also be used. In the tubular hollow fiber format using a rod-type filler a preferred ratio of the membrane inner diameter to the filler rod external diameter is 1.1 to 10 or more preferably 1.2 to 2.

In another configuration the solvent removal membrane could be in a bundle configuration having multiple hollow fiber membranes. Similarly, in the flat membrane format the device may comprise multiple membranes or layers and suitable screen or other material could be added to the flow pathway to improve the transfer to and from the membrane as described in U.S. Pat. No. 4,999,098.

In the embodiment of using the membrane device after chromatographic separation, the delay volume may impact the peak efficiency. In this regard according to the present invention preferably, the ratio of the eluent flow rate (ml/min) (optimized for a given internal diameter of the separator column) to the delay volume (ml) of the evaporator device is expressed in 1/min units as 0.1 to 2000 or more preferably 5 to 200.

When the devices of the present invention are used prior to chromatographic separation, the delay volume only impacts the sample volume and so has no effect on the peak efficiency. It should be noted that when pursuing chemical regeneration of the ion exchange membrane, the pre separation configuration may introduce or concentrate some regenerant ions that can interfere with analysis, in such cases the post separator configuration is preferred.

It should be noted that multiple membrane concentration devices could also be incorporated such as one before the separator for the sample stream concentration and another for concentrating the post-separation stream. Similarly in multi-dimensional applications the concentrator may find applications at multiple locations in the chromatographic pathway. As per the present invention the ion exchange membranes will be in the regenerated form when implemented with ion exchange membranes. With membranes that have, say, hydroxyl groups (diol based non-ion exchange membranes) no regeneration is needed. Another benefit of ion exchange membranes is loss of analyte ions is minimized since the Donnan barrier does not allow transport of ions of the same charge as the membrane barrier. For example chloride cannot be removed from the sample stream flow channel into the gas stream flow channel due to the repulsion effects of the sulfonated cation exchange membrane.

The devices of the present invention operated at preferred sample stream influent flow rates of 1 µL/min to 20000 µL/min. More preferably 10 µL/min to 5000 µL/min and most preferably 10 µL/min to 2000 µL/min.

A stream of hot gas flows on the outside of the fiber membrane serves to a) provide heat for the solvent (water) evaporation and b) continuously remove or sweep out of the removed water vapor. Preferably the flow of the gas stream is counter current to the sample stream flow. Suitable gas streams are inert gases, such as nitrogen or argon, or purified air from conventional sources such as gas tanks or the like. Air could be purified by well known means such as using traps containing Ascarite and Drierite. Gases can be combined with regenerant as described in U.S. Pat. No. 6,425,284.

The exterior of the membrane could be defined by one or more channels that would carry the hot gas flow and the removed moisture. Such channels may have suitable screens or other material that would aid transport of the moisture from the membrane to the gas stream.

The heater can be positioned at any location in the system which raises the gas temperature to the desired level to evaporate solvent in the sample liquid solvent to the desired extent. It could be disposed to heat the gas (a) at the source, (b) in the conduit between the gas source and concentrator gas stream flow channel, and/or (c) in the gas stream flow channel, itself. As will be described, the heater could be part of the concentrator inside the housing or could jacket the housing. Alternatively, it could be a heater for an enclosure in which the concentrator, and/or chromatographic separator is disposed.

Preferred flow rate of the inert gas was chosen based on the gas usage and evaporator performance. It is desirable to keep the gas usage to a minimum. The preferred flow rate of the gas is 0.02 to 10 SLPM (Standard Liter per minute) and more preferably 0.1 to 5 SLPM and most preferably 0.1 to 2 SLPM. The preferred direction of flow is counter current to the sample stream flow however the device could also be operated concurrent with the direction of the sample stream. Preferably the gas temperature is controlled by monitoring the gas temperature at the outlet of the gas stream flow channel.

Preferably the temperature range for the inert gas stream is from room temperature to slightly below the boiling point of the sample stream. For predominantly water containing streams the preferred temperature, measured at the outlet is 30° C. to 90° C. and more preferably 40° C. to 80° C. For other solvents the boiling point needs to be considered when setting the inert gas stream temperature. Preferred operational temperature at the outlet would be approximately 5° C. to 10° C. lower than the boiling point of the solvent of interest. For example the boiling point of methanol is 65° C. and the set temperature would be 55-60° C. The optimal operational temperature could be determined empirically by starting a few degrees below the boiling point of the solvent and slowly lowering the temperature by known increments while monitoring the evaporated sample stream flow rate. Operation at above the boiling point should be avoided since the analytes of interest may be deposited on the membrane. It should be noted that the heating could be turned on or off to invoke evaporation on demand. This will allow tuning the evaporation during a separation. This approach would be particularly useful when pursuing analysis of trace ions in the presence of high levels of matrix ions. Under these conditions, it would be useful to only enhance the sensitivity of the trace ions while keeping the temperature and/or flow of gas off during the elution of matrix ions. Thus selective enhancement of the analyte sensitivity is possible which cannot be done with concentrator columns of the prior art. Therefore it is advantageous to pursue concentration by the present approach in a post separator configuration.

It is believed that the heated gas causes a portion of the solvent, typically water, in or at the interface with the membrane to evaporate and flow through the membrane to be carried away by the flowing gas. Preferably the solvent evaporation rate is greater than 20%, more preferably in the 40% to 95% range. Solvent evaporation rate could be calculated by monitoring the flow into and out of the sample stream flow channel.

Preferably, the temperature of the gas at the outlet is at least about 10° C. higher than the temperature of the incoming liquid sample flowing through the concentrator, preferably at least about 20° C. higher, and more preferably at least about 30° C. higher.

In yet another embodiment the ion exchange membrane is in a flat membrane format. The preferred thickness of the membrane in the dry format is in the 25 µm to 125 µm thick and more preferably in the 50 µm to 125 µm thick.

It should be noted that it is preferable when pursuing anion analysis to use cation exchange membrane and vice versa for cation analysis. Concentration according to this invention also is effective in separation of organic compounds. This way the analytes of interest would not interact with the membrane. Retained ions on the membrane are usually counter ions and require regeneration to ensure even evaporation.

DETAILED DESCRIPTION OF CERTAIN EMBODIMENTS

Example 1

Membrane Tube Based Concentrators

Initial studies on the performance of different membrane devices were carried out using 10 cm lengths of each membrane. FIG. 1 is a schematic of the tubular concentrator. The membrane tube was enclosed in a PTFE tube 20 (6.7 mm id, 7.7 mm od, 80 mm long, Zeus Industrial Products, Inc.). A polyvinyl chloride (PVC) pump tube 10 (190 µm id, 2 mm od, 5 mm long, Cole-Parmer Instrument Co.) was used as a butt-connector between the membrane tube and fused silica capillary 12a or 12b (250 µm i.d., 365 µm o.d., Polymicro Technologies). Arms of ¼" id polypropylene tee 16 (Ark-Plas Products Inc.) was appropriately cut and connected to the PTFE tube for gas inlet/outlet connections. Thus, the tubular membrane 18 is mounted in coaxial external tube 20. The heated gas flows through the annular space therebetween to heat the solvent in the influent aqueous liquid solvent stream. The temperature was monitored with a resistance thermal detector sensor (RTD sensor) 80 at the outlet of the gas flow channel.

Figure 2:
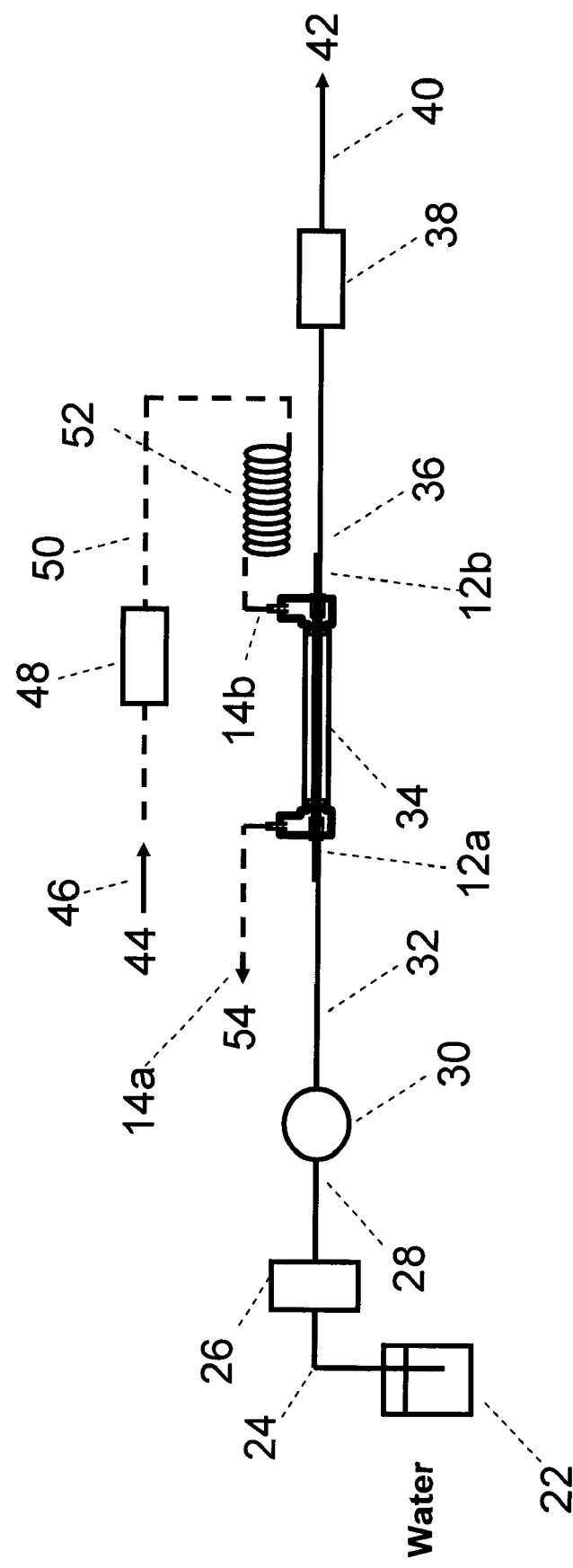
FIG. 2 illustrates an experimental setup for water evaporation measurement using the membrane tube concentrator of FIG. 1.

FIG. 2 is a schematic representation of a test system for the concentrator. Deionized water was pumped through the membrane tube 34 by a syringe pump 26 (model 24520, Kloehn Ltd., Las Vegas, Nev.)) via an inlet 12a and exited the membrane tube at outlet 12b at a flow rate of 5 to 25 µL/min while the membrane 18 was encased in a jacket through which purified air or $N_2$, metered (0.1-2 standard liters per minute (SLPM)) by a mass flow controller 48 (model FC-280, Tylan General) flowed in a countercurrent fashion (to the deionized water flow) via an inlet 14a and exiting at outlet 14b. Sodium nitrate (1 mM, 200 nL) was manually injected by a 4-port injection valve (Type CI4W.2, Valco Instruments Co. Inc.) 30, and the effluent was monitored by a detector 38. An absorbance detector at 210 nm ($CV^4$, ISCO Inc.) or a homemade nongalvanic capacitance/conductance detector (calibrated such that the detector output can be read either in terms of capacitance or conductance, the latter being used here. The entire evaporation device (as well as the conductance detection cell) was housed inside the enclosure of a HPLC column heater (model CH-30, Fiatron Systems Inc; not shown) and this was used to control device temperature. Lengths of copper tubing 52, also located within the heated enclosure allowed for preheating the gas stream.

The following membrane tubes (18) were tested in the concentrator: A and B were cation exchanger membrane tubes that were PTFE based and were radiation grafted with polystyrene monomer and then sulfonated by reacting with sulfuric acid according to a method disclosed in U.S. Pat. No. 4,999,098. The graft levels were 17.8% and 8.2% respectively. Tubing C was a carboxylate functionalized porous polypropylene membrane (Accurel® PP, 400 µm i.d., 508 µm o.d., Enka, Wuppertal, Germany that was pulsed plasma functionalized according to a proprietary process to provide surface —COOH groups. Tubing D and E were Nafion® membranes that were obtained from Perma-Pure LLC, Toms River N.J.), Tubing F was Nafion® coated micro porous polypropylene membrane (Celgard® X-10, 100 µm i.d., 150 µm o.d., Celanese Corp., coating process described in example 2). The membrane tubes 18 tested in the concentrator are listed below.

A) Cation exchanger (graft level 8.2%) 85 µm i.d. 254 µm o.d
B) Cation exchanger (graft level 17.8%) 102 µm i.d. 305 µm o.d
C) COOH functionalized Accurel PP
D) Nafion coated Celgard
E) Nafion 89 µm i.d. 203 µm o.d.
F) Nafion 229 µm i.d. 330 µm o.d

Example 2

Procedure for Coating a Hydrophobic (Celgard) Membrane With a Hydrophilic (Nafion) Coating A length of Celgard membrane was immersed in methanol (Mallinckrodt) and then immersed and withdrawn from a 5% Nafion solution (Aldrich), followed by drying for 12 hours. It was then immersed a second time in the Nation solution and the second coating allowed to dry 12 h before use. By placing a thin coating of hydrophilic layer on top of the porous Celgard membrane the tubing is transformed to a hydrophilic membrane.

Example 3

Maze Concentrator

Figure 3C:
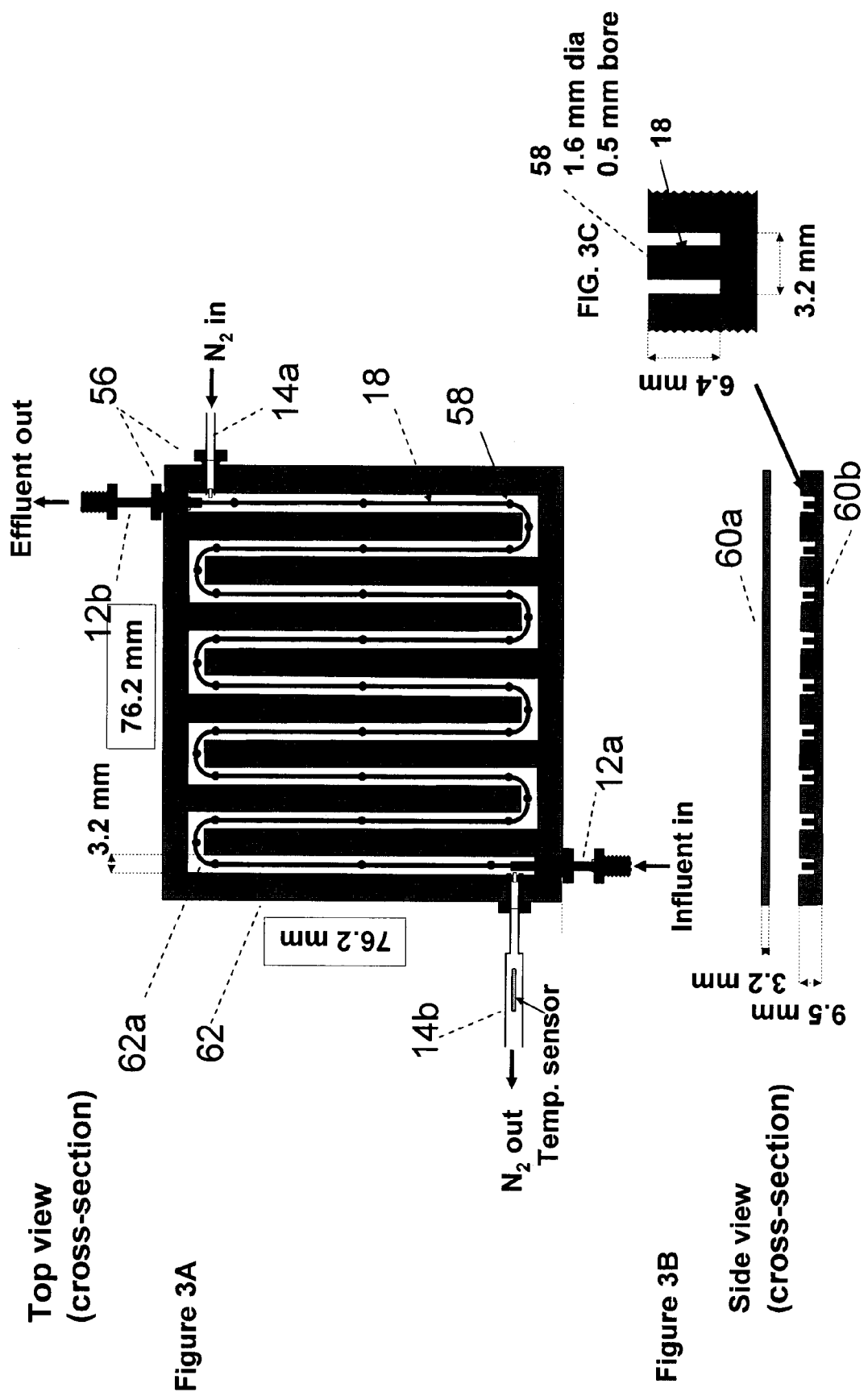

FIGS. 3A-3C schematically show a maze type concentrator in which the membrane tube is in a serpentine path. These devices were built with the Nafion® tubes with an active length of 62 cm. Before assembling the device, the Nafion tube was boiled in 1 M sulfuric acid for 5 min to completely regenerate the tube, and washed thoroughly with water and allowed to dry. The Nafion tube 18 was strung through 0.5 mm apertures in 35 PEEK posts 58 (1/36 in. dia.) that were affixed in recesses in a right angled serpentine maze 62a machined in aluminum block 62. The groove was 6.4 mm deep and 3.2 mm wide. The posts 58 served to prevent the Nafion tube 18 from touching the external walls or crimping at a turn. Both end of the membrane tube (ca. 1 mm) were inserted in a fluorinated ethylene propylene (FEP) tube (159 µm id, 254 µm od, 25 mm long) and 10-32 to 10-32 unions were used at each end for a leak-tight connection (12a and 12b). A resistance temperature detector (RTD) sensor (1PT100KN1515CLA, Omega Engineering, Inc.) was put as close as possible at the nitrogen gas outlet.

Figure 4:
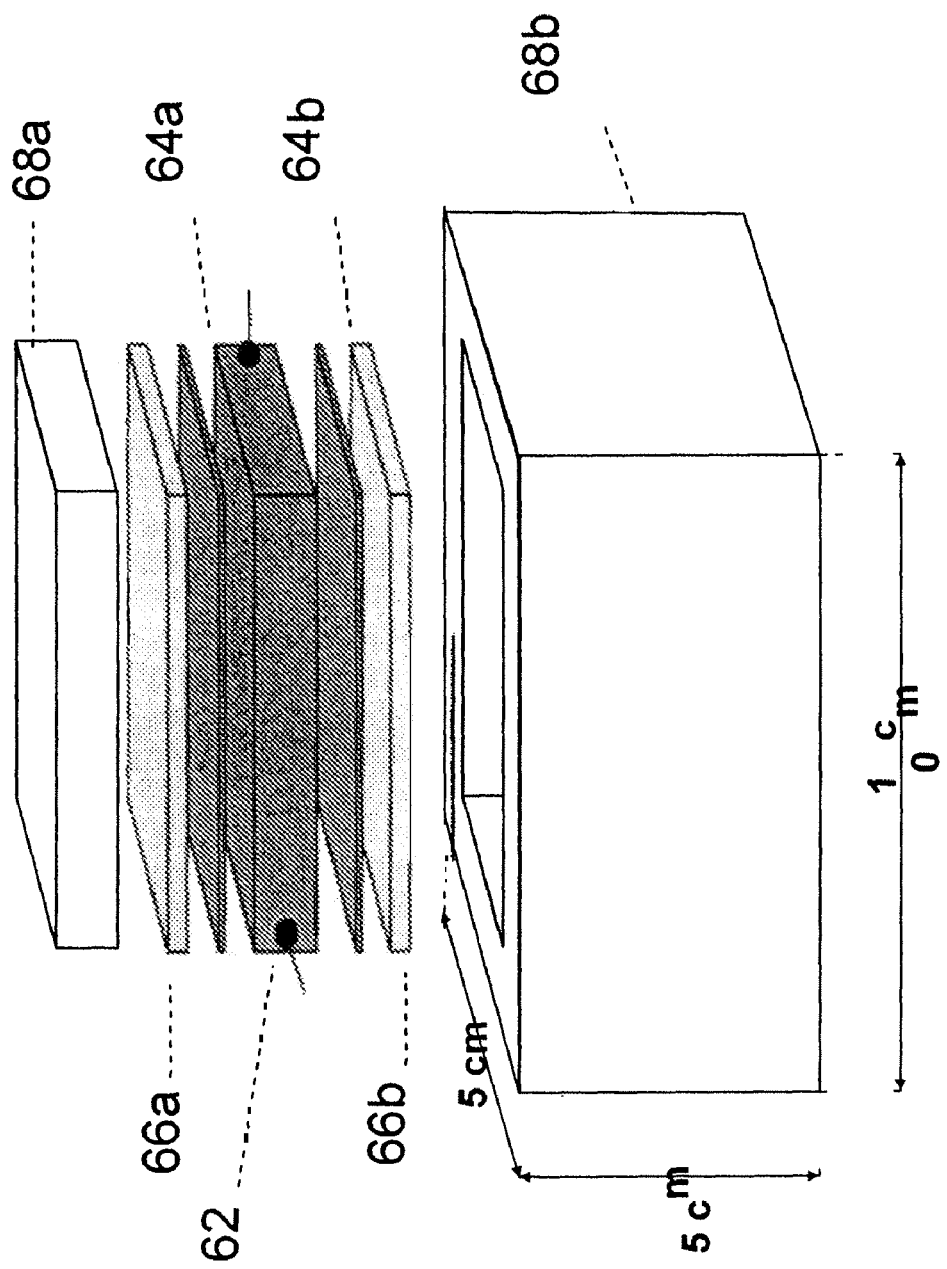
FIG. 4 illustrates a maze type concentrator external packaging.

Referring to FIG. 4, the Al-block 62 was sandwiched with silicon flexible heaters 64a and 64b (75 mm×75 mm, 030030C1, Watlow Columbia, Mo.) and then sandwiched between foam pads 66a and 66b, and placed in an insulating Styrofoam container 68b. A temperature controller (CN8590 1/32 DIN temperature controller, Omega Engineering, Inc.) was used to read and keep desired temperature inside of the maze channel.

In operation, liquid flows through the membrane tube, gas flows through the maze countercurrently, and block temperature is controlled by a temperature sensor placed in the gas exit point.

In order to evaluate water evaporation rate from the membrane tube, 10 µM sulfuric acid was pumped through the maze type concentrator. Water evaporation rate, $W_e$, µL/min was calculated as $$W_e = F_i(1 - C_i/C_e) \tag{1}$$

where $F_i$ is the influent flow rate (100, 200, 300, 400, and 500 µL/min), $C_i$ is the influent sulfuric acid concentration, and $C_e$ is the effluent sulfuric acid concentration calculated from the measured conductance. To assure accuracy, sulfuric acid and pure water were alternately pumped using a two-syringe system. Effect of the drying gas flow was evaluated using air or $N_2$ at a constant 5 SLPM flow with the flow accomplished both by pressure and by vacuum.

Example 4

Helix Concentrator

Referring to FIGS. 5A and 5B, a nylon monofilament (127 µm dia, 62 cm long, Maxima America, Costa Mesa, Calif.) or an acrylic monofilament (VS-100 blue core 50%, 140 µm dia, 62 cm long, Biogeneral Inc., San Diego, Calif.) 90 was inserted into a Nafion membrane tube 18 (229 µm i.d., 330 µm o.d., 62 cm long). The filament-filled membrane tube 88 was coiled around a steel rod (1.27 mm dia), and both tube ends were affixed to the rod with PTFE tape. The entire assembly was immersed in boiling water. After 5 min immersion in boiling water, the heat was turned off, and the device was allowed to remain in the warm water for a further 15 min. The tapes and the helical membrane tube were removed from the steel rod. The helical membrane tube was enclosed in a glass tube 84 (4.1 mm id, 6.1 mm od, 70 mm long), and the end of the membrane tube (ca. 1 mm) were inserted in a FEP tube 76 (159 mm id, 254 μm od, 25 mm long). Arms of ⅛" id tee were cut 78 and connected to the glass tube. A male nut 70 was connected to the tee with an epoxy 91 and external connections for liquid in/out to the helix were made with 10-32 to 10-32 unions 72. A jacketed heating filament 86 (30 cm long, Continental Wire Corp., 120 V, 30W) was coiled around the glass tube. An aluminum tape 82 was wrapped around the heating filament and the jacket to affix the filament as well as for better thermal distribution. A RTD sensor 80 was put in a Teflon tube which was connected to the output of nitrogen flow. The temperature of the device was adjusted by changing applied voltage to the heating filament.

Example 5

Serpentine Concentrator

Figure 6:
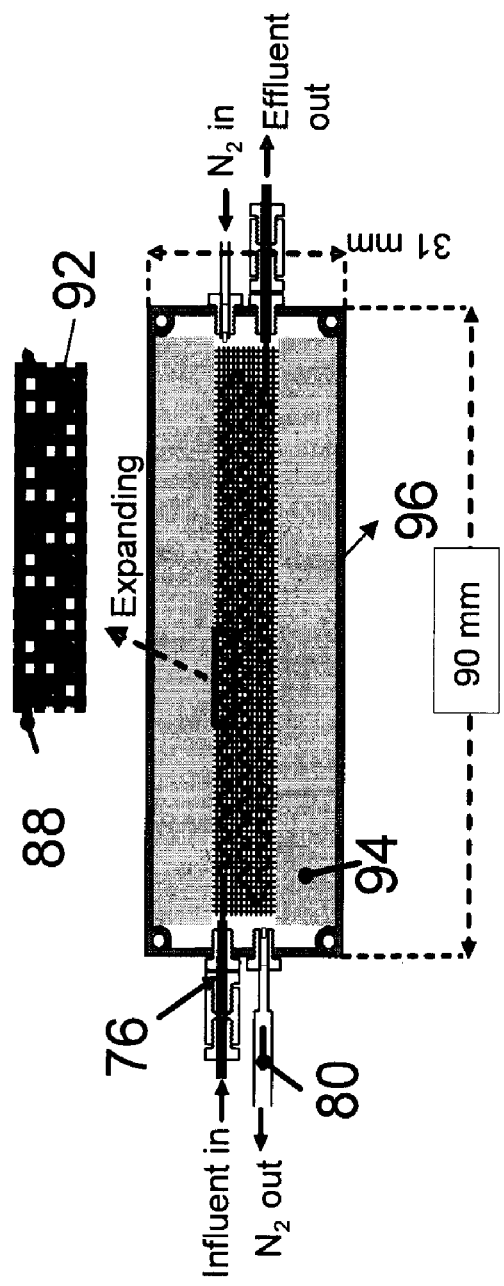
FIG. 6 illustrates a serpentine concentrator.

Referring to FIG. 6, a nylon monofilament (127 μm dia, 62 cm long) filled Nafion membrane tube 88 (229 μm i.d., 330 μm o.d., 62 cm long) was woven on a polypropylene screen mesh cloth 92 (CMP-500, 500 μm mesh opening, Small Parts, Inc.). The end of filament-filled membrane tube (ca. 1 mm) was inserted into a FEP tube 76 (254 μm i.d., 1.59 mm o.d) and external connections for liquid in/out to the helix were made with 10-32 to 10-32 unions. The mesh cloth bearing the woven membrane was embedded within a cavity 94 (77 mm×10 mm×3.5 mm) in conductive foam sheet. The assembly was placed in an aluminum box 96 (top, 90 mm×31 mm×3 mm; bottom, 90 mm×31 mm 10 mm) provided with inlets and outlets for the liquid and nitrogen gas. A 100 cm long heating filament was wrapped around the aluminum box and held in place with adhesive aluminum tape (not shown). An RTD sensor 80 monitored the nitrogen flow exit and was used to control the operating temperature. The entire assembly is shown in FIG. 6.

Chromatographic test arrangements. An ion chromatograph (IC) was operated with the maze, helix, and serpentine type concentrators. Table 1 shows the specific details for each concentrator tested in this manner. The IC system was configured for use as a 2-mm system (GP40 gradient pump 102, 150 μL/min; EG40 eluent generator 104, 21.5 mM potassium hydroxide; LC30 chromatography oven 124, 30° C.; AG11-HC 2 mm guard column 108+AS11-HC 2 mm separation column 110, ASRS ULTA-II 2 mm anion suppressor 112, suppressor current 50 mA, external water mode (200 μL/min); CD20 conductivity detector, all from Dionex Corp.) 120. A sample consisting of a common anion test standard (0.1 ppm chloride, 0.1 ppm nitrite, 0.2 ppm sulfate, and 0.2 ppm nitrate, 25 μl) was used for this system.

Figure 7:
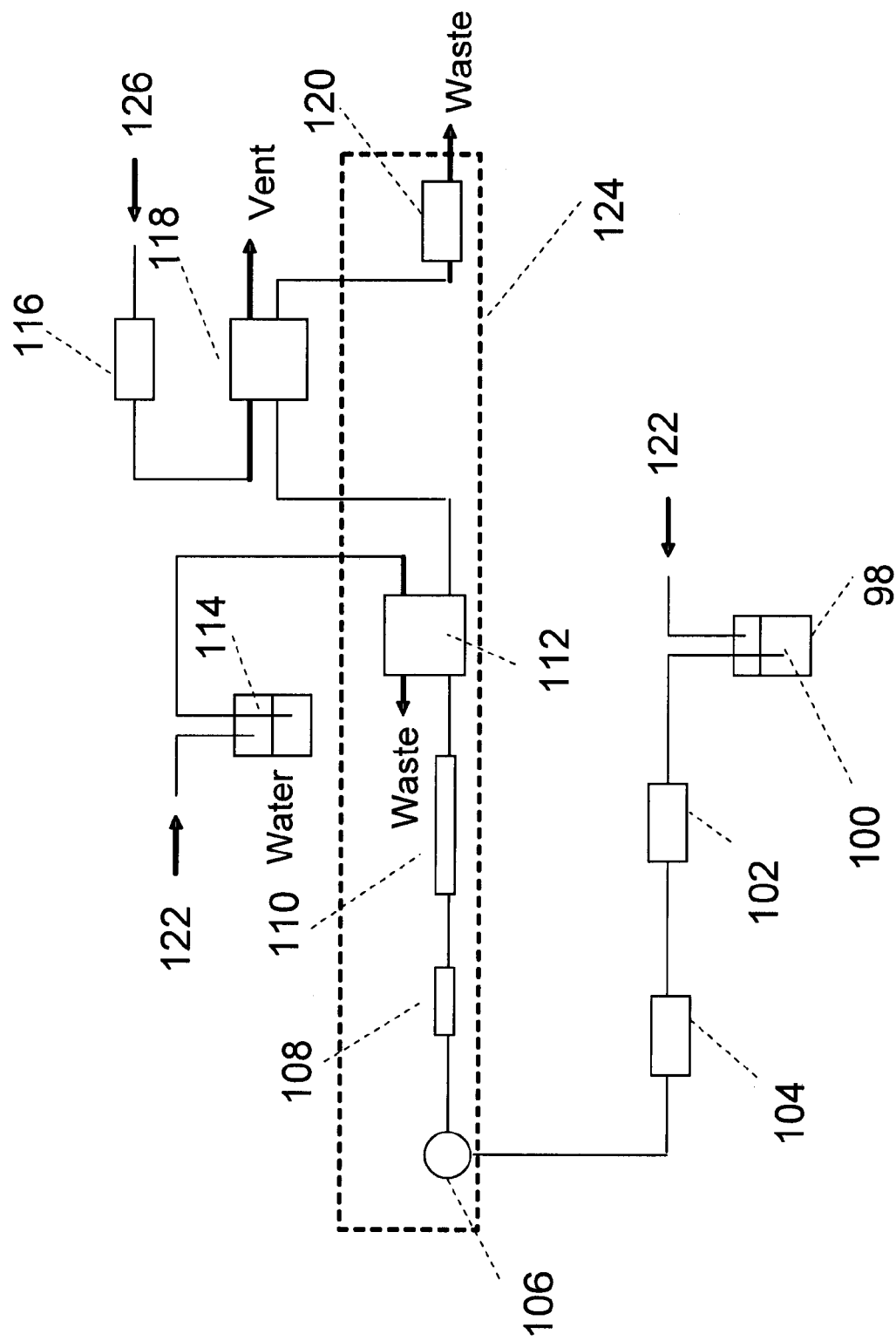
FIG. 7 illustrates a schematic flow diagram of a chromatography system using the concentrator of the present invention.

Referring to FIG. 7, the membrane concentrator 118 was placed downstream from a chromatographic column 110 between an electrolytic membrane suppressor 112 of the type sold by Dionex Corporation under the trademark ASRS and described in U.S. Pat. No. 4,999,098 and conductivity detector 120. In operation DI water 100 was pressurized from a reservoir 98 using gas pressure 122 and the water was pumped by the pump 102 into a high pressure eluent generator (EGC) cartridge of the type sold by Dionex Corporation. The eluent was diverted into the injection valve 106 and then diverted into a guard column 108 and separator column 110 for separating the species of interest. The samples were injected from an autosampler (not shown) or manually injected from the injection valve 106. The effluent from the column 110 was diverted into a suppressor eluent channel in suppressor 112 and then routed into the membrane concentrator 118 via influent port 12a and effluent port 12b (shown in the respective figures). The concentrated analytes are then diverted into a conductivity or suitable detector 120 for detecting the analytes. An inert gas stream preferably N2 126 was pumped at 5 SLPM via a mass flow controller 116 or suitable gas regulator and then diverted into the membrane concentrator 118 via gas inlet port 14a and through gas outlet port 14b in preferably counter current direction to the eluent flow and then diverted to waste.

Water evaporation rate was calculated as difference between influent and effluent flow rate (both were gravimetrically measured). Concentration factor, CF, based on peak height/area was calculated as $$CF = C_w / C_{wo} \quad (2)$$

where $C_w$ and $C_{wo}$ are the analyte peak height or area (area computed in terms of signal intensity.volume, rather than signal intensity.time, as the flow rates varies with/without concentrator, respectively.

Preinjection evaporative concentration of common anions was also studied. (Here, concentration occurs prior to injection into the IC system.) A maze type concentrator was exclusively used. The sample (the same aforementioned common anion standard was continuously pumped through the concentrator by a syringe pump at an influent flow rate of 135-200 μL/min, to fill a 25 μL injection loop, which was periodically injected in to the IC system described above.

TABLE 1

Specification of concentrators.

| Type | membrane tube | Tube i.d., μm | tube o.d., μm | tube wall thickness, μm | tube inner surface, mm² | residence volume, μL | inserted filament | inserted filament dia., μm | Device Designation |
|---|---|---|---|---|---|---|---|---|---|
| Maze | Nafion | 229 | 330 | 51 | 223 | 25.5 | None- | N/A- | I |
| Maze | Nafion | 229 | 330 | 51 | 223 | 17.7 | Nylon | 127 | II |
| Maze | ST708B[a] | 127 | 330 | 102 | 124 | 7.9 | None- | N/A | III |
| Maze | ST741A[a] | 127 | 381 | 127 | 124 | 7.9 | None- | N/A | V |
| Maze | ST708C[a] | 127 | 483 | 178 | 124 | 7.9 | None- | N/A | IV |
| Helical | Nafion | 229 | 330 | 51 | 223 | 17.7 | Nylon | 127 | VI |
| Helical | Nafion | 229 | 330 | 51 | 223 | 16.0 | Acrylic | 140 | VII |
| Serpentine | Nafion | 229 | 330 | 51 | 223 | 17.7 | Nylon | 127 | VIII |

Figure 8:
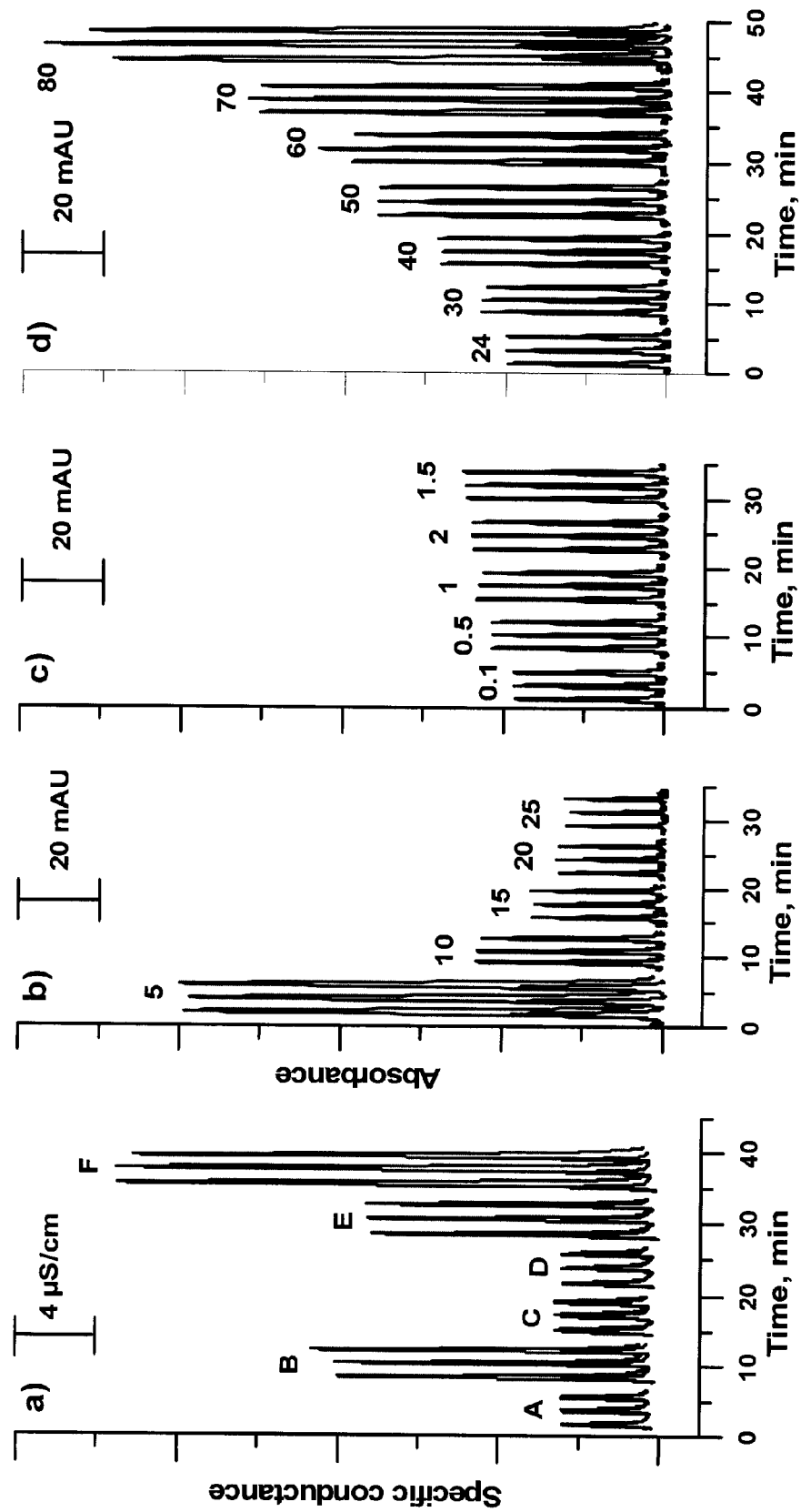
FIG. 8 illustrates a comparison of sodium nitrate peak with (red) and without (black) 10 cm membrane based concentrator. Sodium nitrate was injected 3 times for each experimental condition. All Experiments: unless otherwise noted 10 µL/min influent flow, t=30° C., 5 SLPM $N_2$ flow, Nafion, 89 µm i.d. (a) Effect of membrane tube material: A: cation exchanger Cex ST730, B: cation exchanger Cex ST728, C: —COOH functionalized Accurel PP, D:, Nafion coated Celgard, E: Nafion, 89 µm i.d., F: Nafion, 229 µm i.d. F operated with 3 SLPM $N_2$; (b) Effect of influent flow rate. 5-25 µL/min influent flow rate as indicated, 1 SLPM $N_2$ flow throughout. (c) Effect of $N_2$ flow rate. 0.1-2 SLPM $N_2$ flow rate, as indicated; (d) Effect of temperature: 24-80° C., as indicated; 1 SLPM $N_2$ flow.

The length of all membrane tube was 62 cm.
[a]Radiation-grafted PTFE-based Cation exchange membrane Results and Discussion Effect of membrane type and operating variables. The performance of different membrane tubes and the effect of operating parameters such as influent flow rate, drying gas flow rate, and temperature was evaluated using the short (10 cm) straight tubular membrane concentrators (FIG. 1) Results for six different membrane devices are shown in FIG. 8a under otherwise comparable conditions. One radiation-grafted cation exchanger membrane tube with lower graft level of 8.2% showed negligible evaporation, however, the other with higher graft showed evaporative concentration. The higher graft level ensures higher number of functional groups on the surface of the membrane making it more hydrophilic. Note that some dispersion is unavoidable when an evaporation device is connected; as such if there is little or no evaporation, peak heights will actually decrease due to the added delay volume This is indeed observed for the Nafion® coated Celgard® tube (D). Further studies with radiation grafted cation exchangers (vide infra) were limited to ones with higher ion exchange capacities and all showed substantial evaporative concentration. Evaporative concentration with the —COOH functionalized polypropylene tube is discernible but small. This coating technique results in relatively thick coatings and little evaporation occurs. In contrast, both Nafion® tubes show significant evaporative concentration. The extent of evaporative concentration was much greater for the larger bore tube. This is to be expected inasmuch as compared to the smaller membrane tube (E, 89 µm id, 57 µm wall), the larger tube (F, 229 µm id, 51 µm wall) had about the same membrane thickness and 2.6× greater inner surface area and 6.6× greater residence volume. In fact the data for the larger tube are presented with a smaller drying gas flow rate because with the same gas flow rate of 5 SLPM, liquid evaporation was so extensive that at best the liquid reached the detector intermittently, resulting in severe noise.

Many of the paradigms considered as axiomatic regarding flow through tubular conduits break down when evaporative loss occur through the tube walls. This is because flow rate through the tube changes along the length of the tube and residence time is no longer linearly related to the residence volume. For the larger tube, volumetric evaporation rate per unit length is larger than that for the smaller tube. As a result, flow rate decreases at a steeper rate than that in the smaller tube and under otherwise identical conditions, residence time in the larger tube is greater than what the ratio of the internal volumes will indicate. In a similar vein, for tubes of identical bore, residence time is more than linearly proportional to the length of the tube. The departure from the linear model is obviously greater as a greater fraction of the influent liquid is subjected to loss, for a situation where the influent flow is large and only a small portion of this liquid evaporates, the system will behave close to the conventional model.

Thus, in the low influent flow rate range of 5-25 µL/min, with the extent of evaporation of the influent flow being significant, the ratio of peak height with/without the concentrator increased not linearly but exponentially as the influent flow rate was decreased. This is readily visible in the data of FIG. 8b. Note that while conductance was monitored in FIG. 8a, the other panels in FIG. 8 used absorbance detection, any concentration-sensitive detector will similarly respond to the concentration gains attained through evaporative concentration.

The gas flow serves to remove the water vapor that emanates from the membrane tube. At 30° C., each L of water vapor saturated $N_2$ holds ~8.6 µL of liquid water. As such, flow rates higher than about 1.2 SLPM aids primarily to diffuse away the water vapor emanating from the membrane surface. As such, this behavior should be governed by a relationship akin to the Gormley-Kennedy equation for flow through a cylindrical tube ([4]) where a plateau is exponentially approached. This behavior is indeed seen in FIG. 8c over a drying gas flow rate range of 0.1-2 SLPM.

Temperature plays of course perhaps the most vital role in determining the amount of the water lost through evaporation. The rate of loss of water should be linearly related to the water vapor pressure and the vapor pressure of water increases rapidly with temperature. With increasing temperature, the extent of evaporative concentration increased dramatically as shown in FIG. 8d. The ratio of the sodium nitrate peak height with/without concentrator with the vapor pressure of water exhibited an excellent linear correlation ($r^2$=0.9920, t=22-80° C.).

Choice of a Membrane. Several membranes other than those already discussed above were investigated for evaporative preconcentration for which data are not presented in detail. This included (a) a radiation grafted PTFE anion exchanger (Aex 88, 72 µm i.d., 216 µm o.d., Dionex Corp.), (b) a porous Celgard® polypropylene membrane (200 µm i.d., 250 µm o.d., 40% surface porosity) and (c, d) similar polypropylene membranes (209 µm i.d., 263 µm o.d., and 400 µm i.d., 460 µm o.d., coated with a very thin layer (~1 µm) of plasma polymerized polydimethylsiloxane, similar to silicone coated Celgard membrane tubes described in [5]). At 30° C. and 5 SLPM $N_2$ flow, the water loss rates were respectively (a) 0.22, (b) 0.23, (c) $0.08_3$, and (d) 0.19 µL/min/cm, all of which are substantially lower, for example, than 0.93 µL/min/cm observed for the hollow Nafion tube (229 µm i.d., 330 µm o.d.). Of these, only the anion exchange membrane tube has a much smaller bore than the comparison standard and this may produce comparable evaporation if used in a comparable dimension. Anion exchange membranes cannot of course be used for evaporative concentration in suppressed anion chromatography as analyte anions will be captured. However, such a membrane will be of interest in dealing with cationic (as well as neutral) analytes. For the cation exchangers, it appears that the extensive solvation of the hydrogen ion present in such an exchanger plays a paramount role; this will be examined again in a later section. Strong acids in ionized form cannot pass through a negatively charged cation exchange membrane, although weak acids in molecular form are not subject to the Donnan barrier. Thus, cation exchange membranes would be the basis of preferred concentration devices in anion analysis, anyway. With porous membranes the extent of transport to and from the membrane is expected to be a function of fractional surface porosity, pore tortuosity and membrane thickness ([6]). Interestingly, the evaporation rate through the porous Celgard® membrane was not as high as that of the better cation exchanger membranes. This type of membrane also require maintenance in that pores can be gradually blocked by evaporating solids ([6]); coating with a thin asymmetric layer, e.g., of siloxane, may obviate pore blockage but it did not improve water transport rates. Henceforth we used cation exchange membranes the preferred membranes as per the present invention.

Figure 9:
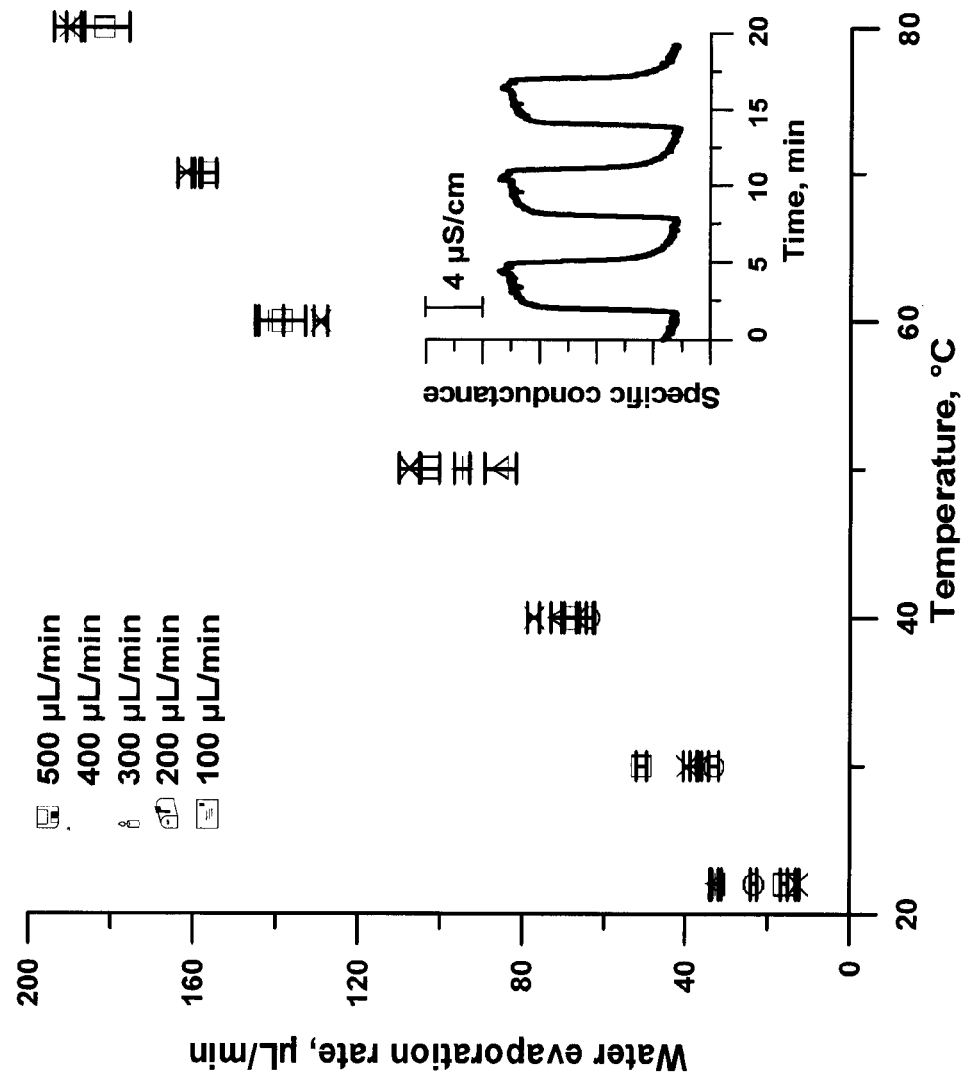
FIG. 9 illustrates water evaporation rate with Nafion membrane tube based maze type concentrator as a function of temperature and influent flow rate, 5 SLPM of nitrogen, n=3. The inset graph shows the typical output when water and 10 µM sulfuric acid flow alternately at 100 µL/min, 30° C. Water evaporation rate was calculated by eq. 1.

Water evaporation as a function of influent flow rate. One would expect that in the absence of significant dissolved solute concentrations, as long as the influent rate is sufficiently high, the absolute amount of water evaporated would be the same, regardless of the precise influent flow rate. This was largely observed for a 62 cm long Nafion tube (229 µm i.d., 330 µm o.d.) in the maze concentrator for an influent flow rate range of 100-300 µL/min. Detailed results are presented in FIG. 9. There was no consistent pattern of evaporation rate change with the influent flow rate but it increased monotonically with temperature as in FIG. 7d. Over the flow rate range of 100-500 μL/min, the average±sd (n=3) water evaporation rates in μL/min were, respectively: 23.5±9.2, 39.6±6.7, 68.9±5.6, 97.6±9.6, 136.7±6.6, 159.6±2.7 and 187.4±4.6 at 22, 30, 40, 50, 60, 70 and 80° C. (the latter four data points do not include the 100 μL/min influent flow rate, for obvious reasons). These data fit a linear pattern:

$$\text{Evaporation Rate (μL/min)}=2.9\pm0.08(t\,°\text{C.})-(44.94\pm4.44),\ r^2=0.9960 \quad (2)$$

Stripping gas flow. Even if the mass flow rate and temperature of the drying gas is maintained the same, it is interesting that the exact arrangement for the gas flow makes a difference whether the drying gas flow is supplied by a positive pressure or by applying a vacuum. In the latter case, outside the membrane the pressure is negative relative to ambient, increasing the pressure differential across the membrane and thus enhancing evaporation. The difference is easily perceptible but it is not large. For the same maze concentrator described in the paragraph above operating with 100 μL/min influent flow and t=40° C., 5 SLPM $N_2$ flowing under pressure and under vacuum resulted in respective evaporation rates of 64.2 and 72.9 μL/min. However, all other data reported here were obtained under pressurized gas flow, as the necessary arrangement is obviously simpler.

Ionic form of the membrane makes a large difference. In a suppressed IC system the concentrator device can be placed after the column, either before, or after the suppressor, prior to the detector. The advantage of placing it upstream of the suppressor is that one is dealing with an alkaline eluent stream with analyte bands that are present as salts and there is no possibility whatsoever of any analyte loss. The precise original ionic form the cation exchange membrane of the concentrator will be immaterial as it will rapidly be converted to the ionic form of the eluent cation. Interestingly, no increase in peak heights was observed at all when the maze type concentrator described above was used in a chromatographic system and placed before the suppressor, even with an 80° C. device temperature. Other experiments confirmed that the membrane preferably is in $H^+$-form for the most significant evaporative concentration. This suggests that the high affinity of the proton for water and the ability of the positive charge to easily tunnel from one water cluster to another ([7]) may substantially account for the high evaporation rates observed for these membranes that are indeed greater than those observed for comparable porous membranes.

Figure 10:
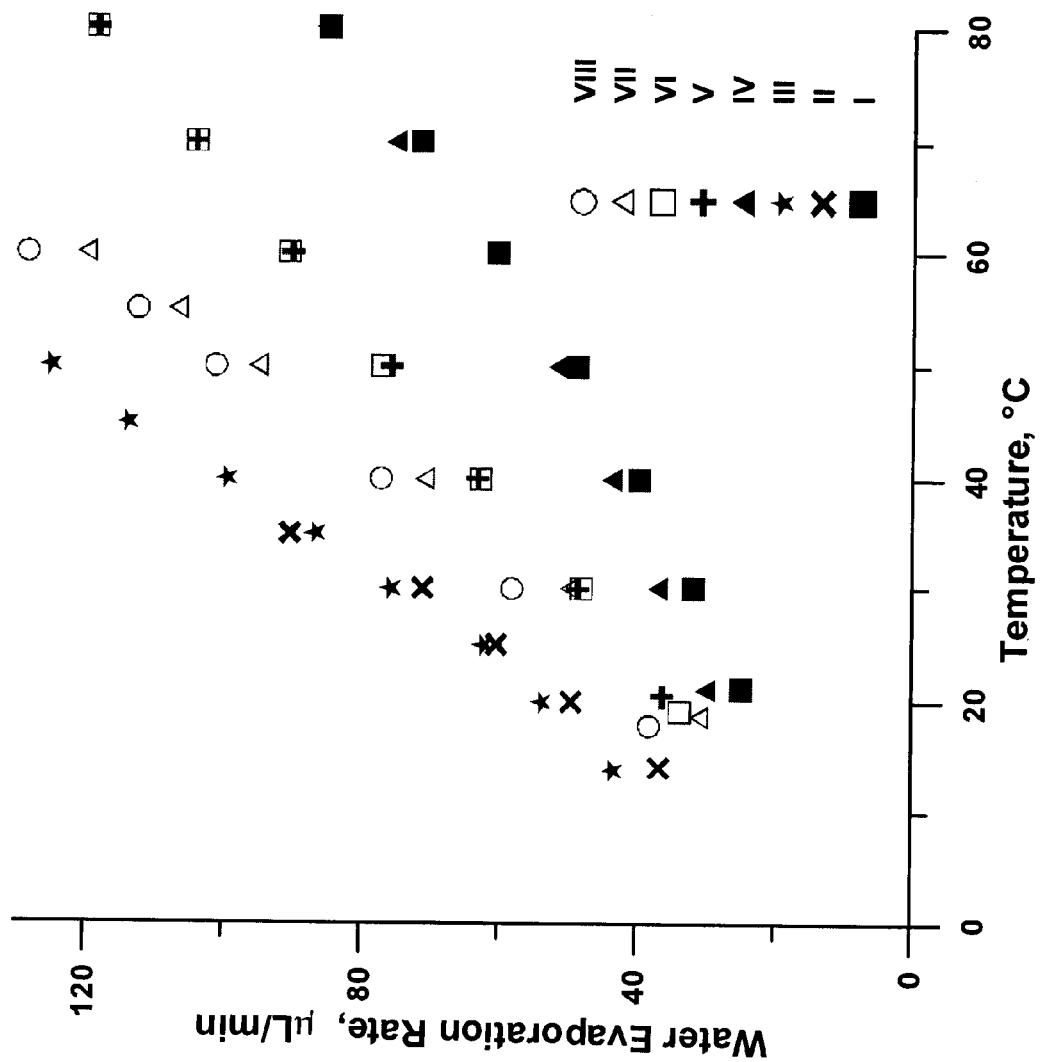
FIG. 10 illustrates a comparison of water evaporation rate between maze, helical, serpentine type concentrator at 150 µL/min, 5 SLPM of nitrogen. Water evaporation rate was calculated as (influent flow rate)-(effluent flow rate). See Table 1 for Device specifications.

Chromatographic application. Postcolumn deployment of a maze/helix/serpentine concentrator. The water evaporation rates for maze, helix, and serpentine concentrators are shown in FIG. 10 as a function of device temperature with a constant membrane length of 62 cm, a drying gas flow of 5 SLPM $N_2$ and an influent flow of 150 μL/min. In all cases, if simply operated at room temperature without active thermal control, the exit gas temperature was several degrees cooler than the entry (room) temperature due to adiabatic evaporative cooling. The water evaporation rate increased in the order serpentine, maze, helix concentrators. In the first design, a good portion of the membrane is in contact with the support grid and evaporation from this area is inhibited. The serpentine design leads to good mass transfer in the flowing liquid, leading to good band dispersion characteristics ([8]), but previous applications did not have any need for good mass transfer outside the tube, which, obviously is a limitation in the present application. The filament-filled helix also leads to leads to good mass transfer in the flowing liquid and hence good band dispersion characteristics ([9,10]) but externally it is suspended in space and mass transfer away from the membrane is not inhibited.

Figure 11:
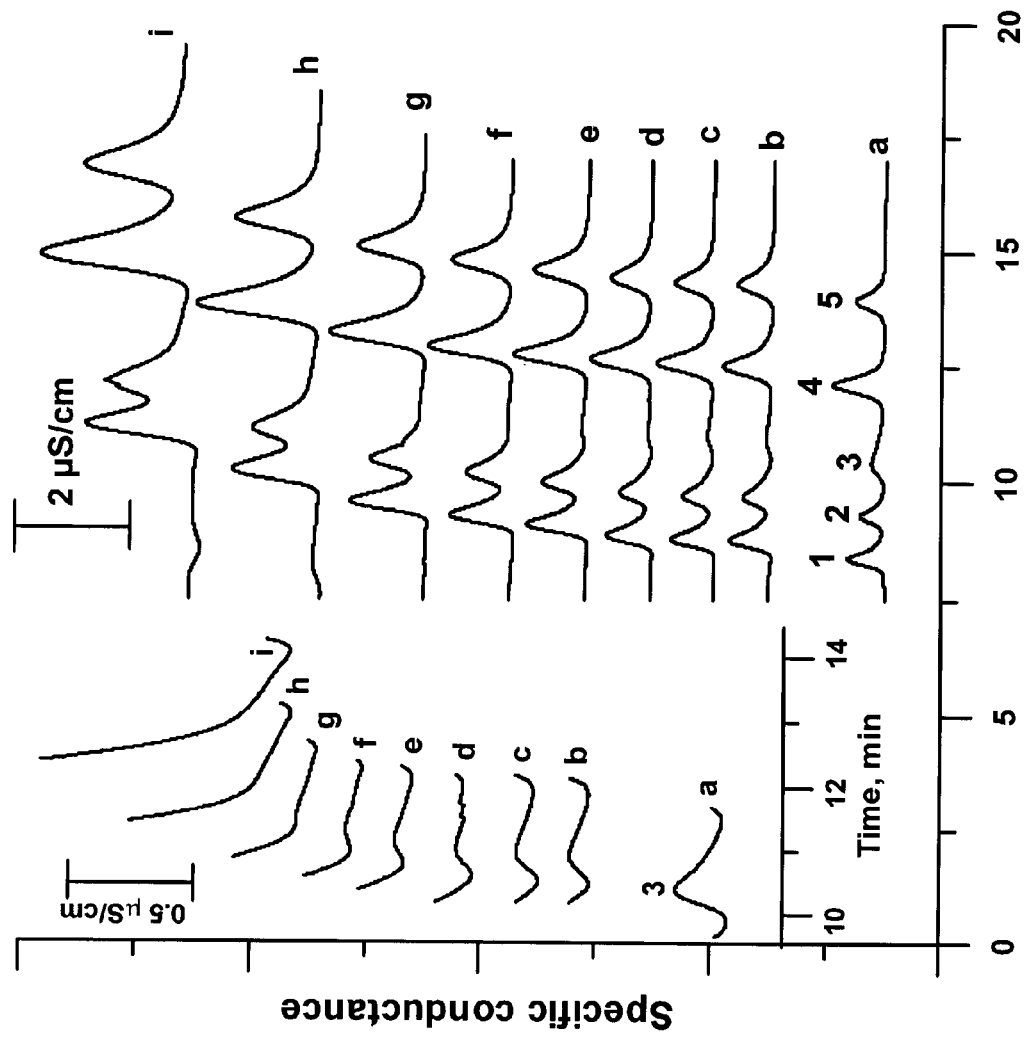
FIG. 11 illustrates a chromatogram with postcolumn concentration with nylon filament-filled Nafion helix concentrator (Table I, Device VI), chromatographic flow rate 150 µL/min, 5 SLPM $N_2$ drying gas. (a) without concentrator, (b) gas exit temperature 14° C., (c) 20° C., (d) 25° C., (e) 30° C., (f) 35° C., (g) 40° C., (h) 45° C., and (i) 50° C. 1) chloride, 2) nitrite, 3) carbonate, 4) sulfate, 5) nitrate. The insert graph shows the response around the original carbonate peak.

FIG. 11 shows the chromatogram with nylon monofilament filled Nafion helix, which demonstrated the highest water evaporation rate. (Note however, the radiation grafted cation exchangers shown in B, have a much smaller bore and if we were to compare on the basis of induced dispersion, these will outperform the Nafion tubes). The peak heights of chloride, nitrite, sulfate, and nitrate increased dramatically with temperature. However, the peak widths (in terms of time) also increased and there was deterioration of resolution. Part of this is due to the relatively long and large bore (30 cm, 0.254 mm) transit conduit between the evaporator exit and the detector. It is also useful to note that the carbonate peak decreases in the membrane concentration process and essentially disappeared at the higher temperatures, as shown in the inset of FIG. 11. It is well known that the broad carbonate peak, often present in a large concentration in samples exposed to ambient air, poses a problem in the trace determination of certain inorganic anions with IC. In particular, when atmospheric trace gases are measured with IC, the broad tailing of carbonate peak covers the response of other ions that elute in this region ([11]). The concentrator therefore is useful also for reducing carbonate response.

Figure 12:
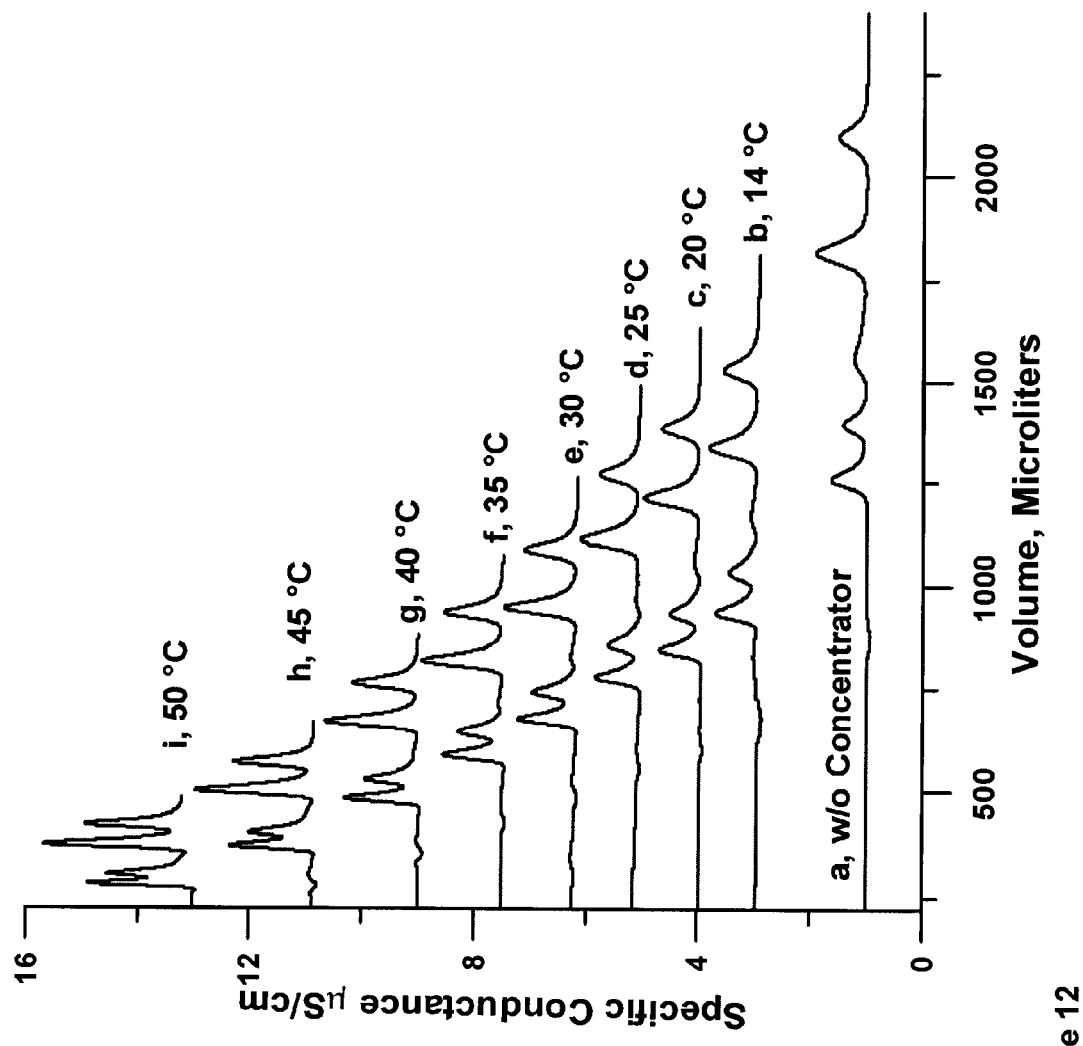
FIG. 12 illustrates a chromatogram of FIG. 5, plotted with volume abscissa.

While FIG. 11 has depicted the chromatograms with the traditional time units as abscissa, this does not give one the whole picture when the individual flow rates through the detector from the top to the bottom chromatogram change by a factor of 6. FIG. 12 shows the same chromatograms with a volumetric abscissa scaling. Interestingly, if one computes the peak resolution of sulfate and nitrate between 14° C. and 30° C., the resolution in fact remains unchanged. Band dispersion originates in the parabolic velocity profile of laminar flow where the velocity at the wall boundary layer is zero. How and to what extent the velocity profile in a tube, which has significant mass flux to the wall, is altered from traditional laminar flow is an interesting question; to our knowledge, such a system has never been studied.

Figure 13:
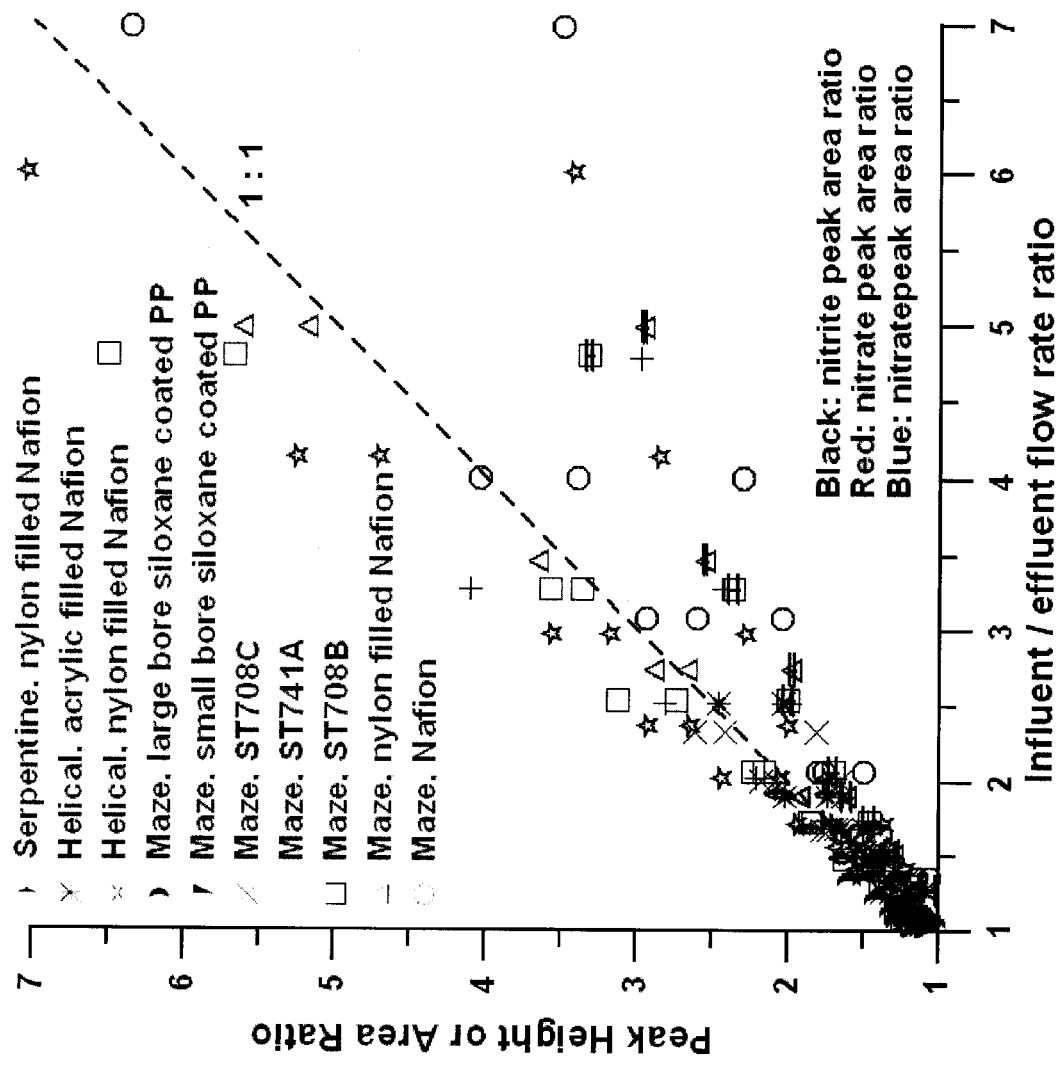
FIG. 13 illustrates the relationship between the peak height and area ratios vs. the influent to effluent flow rate ratio.

Concentration factor based on peak height and area ratios vs. influent/effluent flow rate ratios: loss of analyte. The concentration factor CF (eqn. 2) can be calculated either in terms of height or area ratios. FIG. 13 shows that while the height-ratio based CF for the nitrate peak rapidly departs from the gravimetrically measured influent/effluent flow rate ratio due to dispersion, the area ratio (where the area is based on volume, see eqn. 2), remains linear with the influent/effluent flow rate ratio; indicating that no loss of nitrate occurred during evaporative concentration. This is clearly not the case for carbonate which produces the weak volatile carbonic acid in the suppressor; it can be totally lost during such concentration, which is another unexpected benefit of the present approach. Area ratio data are also plotted in FIG. 13 for an analyte derived from an acid from intermediate $pK_a$, nitrite; these data do not indicant any significant loss of nitrous acid. It remains to be established at what precise combination of volatility and $pK_a$ analyte loss, such as that observed for $CO_2$/carbonate, occurs.

Other detectors. These types of postconcentrators will benefit mass-sensitive detection, particularly with chip-based nanospray modules (www.advion.com) which work with very high efficiency but only at very low flow rates. The present approach is also expected to benefit detection methods such as amperometry which is not only concentration sensitive but also mass-transport dependent, the latter being more efficient at a lower flow rate.

Figure 14:
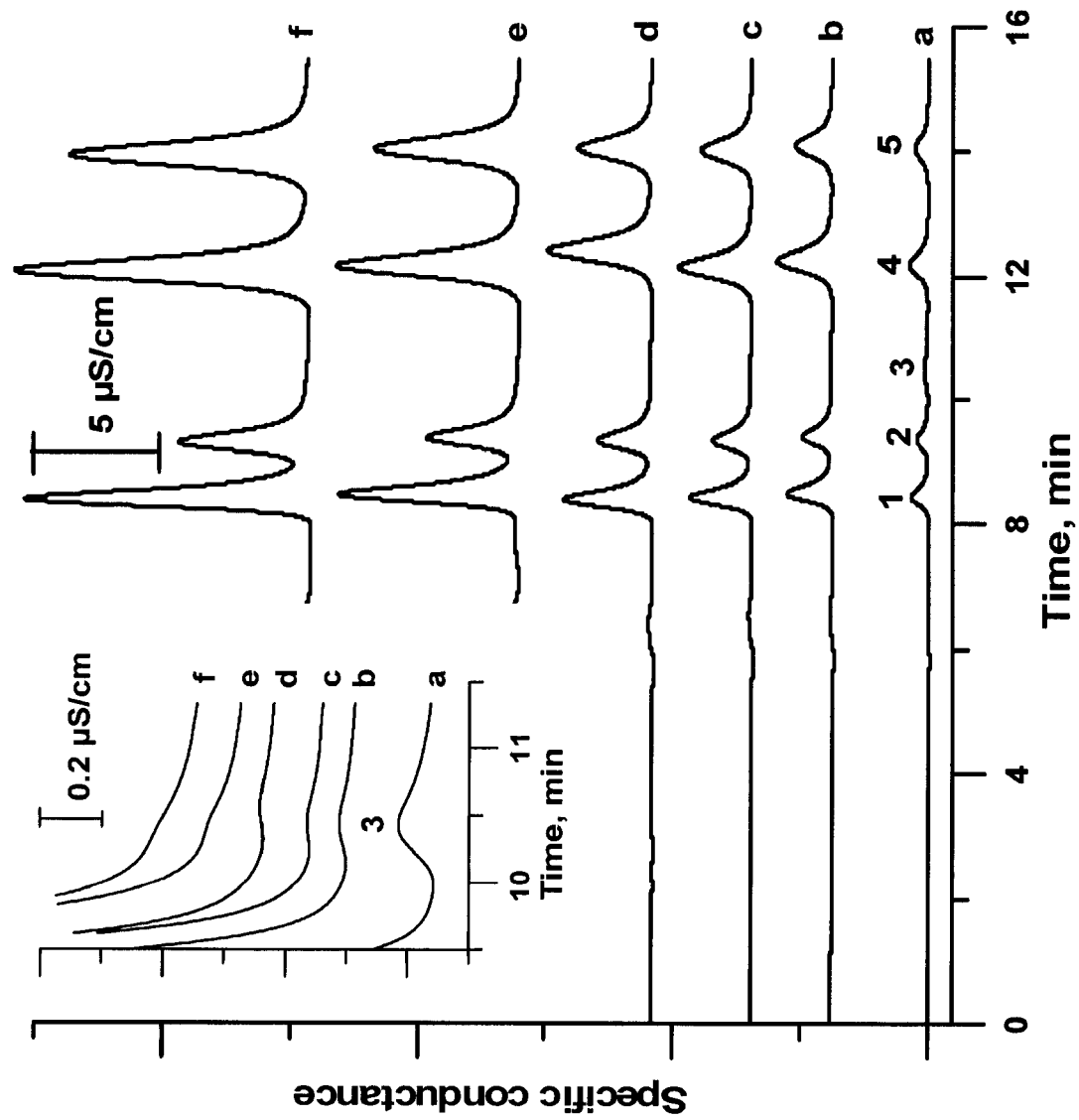
FIG. 14 illustrates a chromatogram of precolumn concentration with Nafion membrane tube based maze type concentrator at 5 SLPM of nitrogen, 60° C. a) without concentrator, b) 200 µL/min, c) 170 µL/min, d) 150 µL/min, e) 140 µL/min, f) 135 µL/min. 1) chloride, 2) nitrite, 3) carbonate, 4) sulfate, 5) nitrate. The inset graph shows extended figure around peak 3.

Preinjection concentration. The evaporative concentration technique can of course be used in the preinjection mode as well. The technique is ideally suitable for use with continuous process analysis of high purity water, for example. FIG. 14 shows the chromatograms obtained with loop injection of a sample that has passed through an evaporative concentrator (Device I, Table I) at different flow rates prior to loading a sample loop. The peak heights of chloride, nitrite, sulfate, and nitrate increased dramatically with decreasing sample flow rate, with no effect on chromatographic resolution. As with postsuppressor use, the response from carbonate decreased significantly with the membrane concentrator.

Figure 15:
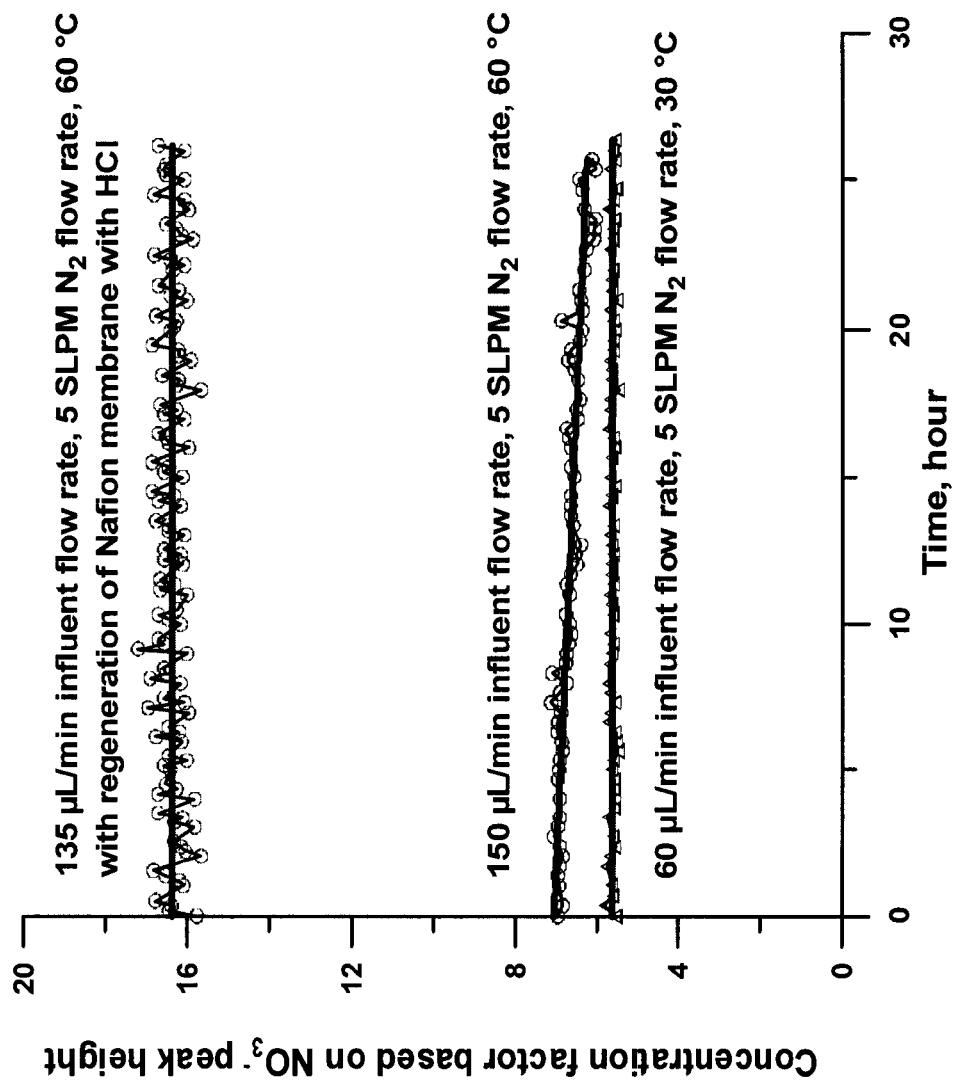
FIG. 15 illustrates a time variation of concentration factor based on nitrate peak height with a maze type concentrator

A possible problem with this mode of concentration is that the samples will generally contain non-$H^+$ cations that will be captured by the membrane. As the membrane is converted from the $H^+$-form to some other cationic form, the water transport properties of the membrane will change and the extent of evaporative concentration achieved will decrease. FIG. 15 shows the decrease in CF (6.90 at the beginning) as a function of time (6.04 after 24 h of continued injections every 20 min). Similar losses in the CF of other anions were observed as well. In order to prevent the membrane significantly converting to a non-$H^+$ form, one may of course pass the sample through a suppressor before the evaporative concentrator. Alternatively the same evaporation membrane device can be periodically regenerated after several injections. After every 4 sample injections 4 mM HCl was pumped in to the concentrator at 0.7 mL/min for 1 min by a peristaltic pump, followed by, water wash at the same flow rate for 19 min to wash out the regenerant. Then, the sample concentration process and injection was recommenced. Residual chloride peak (0.030 μS/cm) was only marginally higher than the blank chloride response (0.021±0.002 μS, n=3). Of course, a strong acid regenerant such as methanesulfonic acid, where the corresponding anion is generally not an analyte of interest, can also be used. In some cases, it may be preferable to alternate between two concentrators. Using the above periodic regeneration protocol, results for nitrate for 24-h continuous operation of the concentrator (influent sample flow rate 135 μL/min, t=60° C. is shown in FIG. 14. The CF for all the ions (nitrate: 16.4±0.3, chloride: 16.5±0.3), nitrite: 12.0±0.2, and sulfate: 14.7±0.3) remained constant over 24 h.

We have observed that the water transport variation between the $H^+$-form of Nafion and other cationic forms is more pronounced at higher temperatures than at lower temperatures. In this vein, we also operated the concentrator at 30° C. with a sample flow rate of 60 μL/min to still maintain a relatively high CF. The CF loss for nitrate was reduced to only 0.3%/day. The CF losses of other ions was 0.5% for chloride, 0.0% for nitrite, 1.1% for sulfate, and were much better than at 60° C. However, the precise performance will obviously depend on the cationic composition of the sample and periodic regeneration as per the present invention will result in reproducible performance.

Example 6

Figure 16:
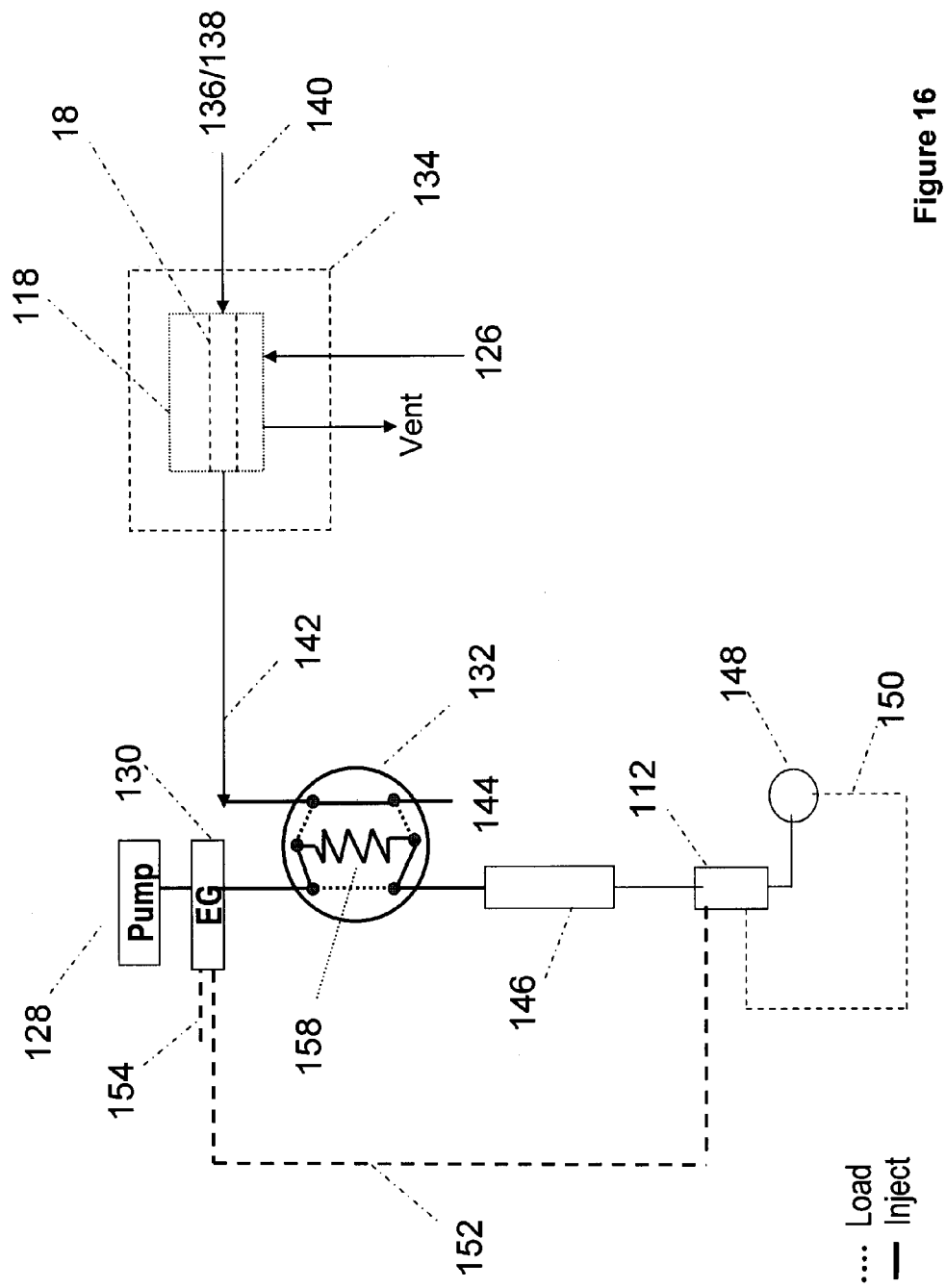
FIGS. 16-22 illustrate chromatographic systems using concentrators according to the present invention.

One embodiment of the present invention is shown in FIG. 16. The instrumental setup consisted of an ion chromatography system sold by Dionex Corporation, Sunnyvale, Calif. and comprising an analytical pump GP50 (128), Eluent Generator Module (130) injection valve (132) fitted with an injection loop (158) or with a concentrator column at the same location (not shown), an analytical column (146) sold under the tradename IonPac from Dionex Corporation, Sunnyvale, Calif. a suppressor sold under the tradename SRS, a conductivity cell (148) a conductivity detector (not shown) and as per the present invention a membrane concentrator (118) with a preferred hydrophilic membrane (18), a thermal compartment such as I,C30 sold by Dionex corporation, Sunnyvale, Calif. or heating means (134) a gas source (126) and a sample source (136) and regenerant source (138). Both the sample and the regenerant can be typically supplied from an autosampler module of the type AS sold by Dionex Corporation Sunnyvale, Calif.

In operation the sample is pumped into the membrane 18 using conduit 140 and after evaporation the evaporated sample is diverted to the injection valve 132 via conduit 142. The sample is loaded onto the sample injection loop 158 in the injection valve 132. The excess sample is diverted to waste 144. On the IC system side, during the sample load step the pump is pumping DI water into the Eluent generator system 130 and the generated eluent is diverted via the injection loop into the chromatography column 146 and then the eluent is diverted into the suppressor 112 where the eluent is suppressed and the suppressed eluent is diverted into conductivity cell 148 for detection. The cell effluent is diverted via conduit 150 back into the suppressor regenerant channel for supplying the suppressor regenerant (water) and then the waste from the suppressor is diverted back to waste or via conduit 152 to the EGC module for supplying regenerant flow for the EG degas module (not shown). During the injection step the eluent is diverted into the sample injection loop 158 and displaces the evaporated sample and the sample is routed to the chromatography column for analysis. The separated sample components are detected by the conductivity cell (148).

The gas source 126 provides pressurized gas to the membrane gas flow channel. The gas is heated in the gas flow channel since the entire chamber is heated from the outside. When an ion exchange membrane is used for membrane 18 the cation exchange membrane during anion analysis can get contaminated with cations from the sample and as per the present invention the evaporation function is affected by this conversion of the membrane to the cation form. The present invention solves this problem by invoking a regeneration step with acid regenerant 138 which is pumped into the cation exchange membrane in a batch mode. The sample flow is discontinued and the regenerant acid flows through the conduit 140 thru the interior channel of membrane 18 and is then routed through 142 to waste 144. The acid converts the membrane 18 back into the hydronium form thereby facilitating evaporation as per the present invention. After the regeneration is accomplished the lines 140 thru interior of 18, thru 142 and to waste is rinsed with DI water to remove any residual acid regenerant. The setup is now suitable for concentrating the next samples. With samples containing high levels of cations the regeneration is recommended after every run. For relatively lower levels of cations during anion analysis the regeneration step should be invoked after several runs. For some samples such ultra pure water samples the cation levels are lower and the regeneration would be needed after several hundred runs. For non ion exchange based hydrophilic membrane no such regeneration is needed.

Example 7

Figure 17:
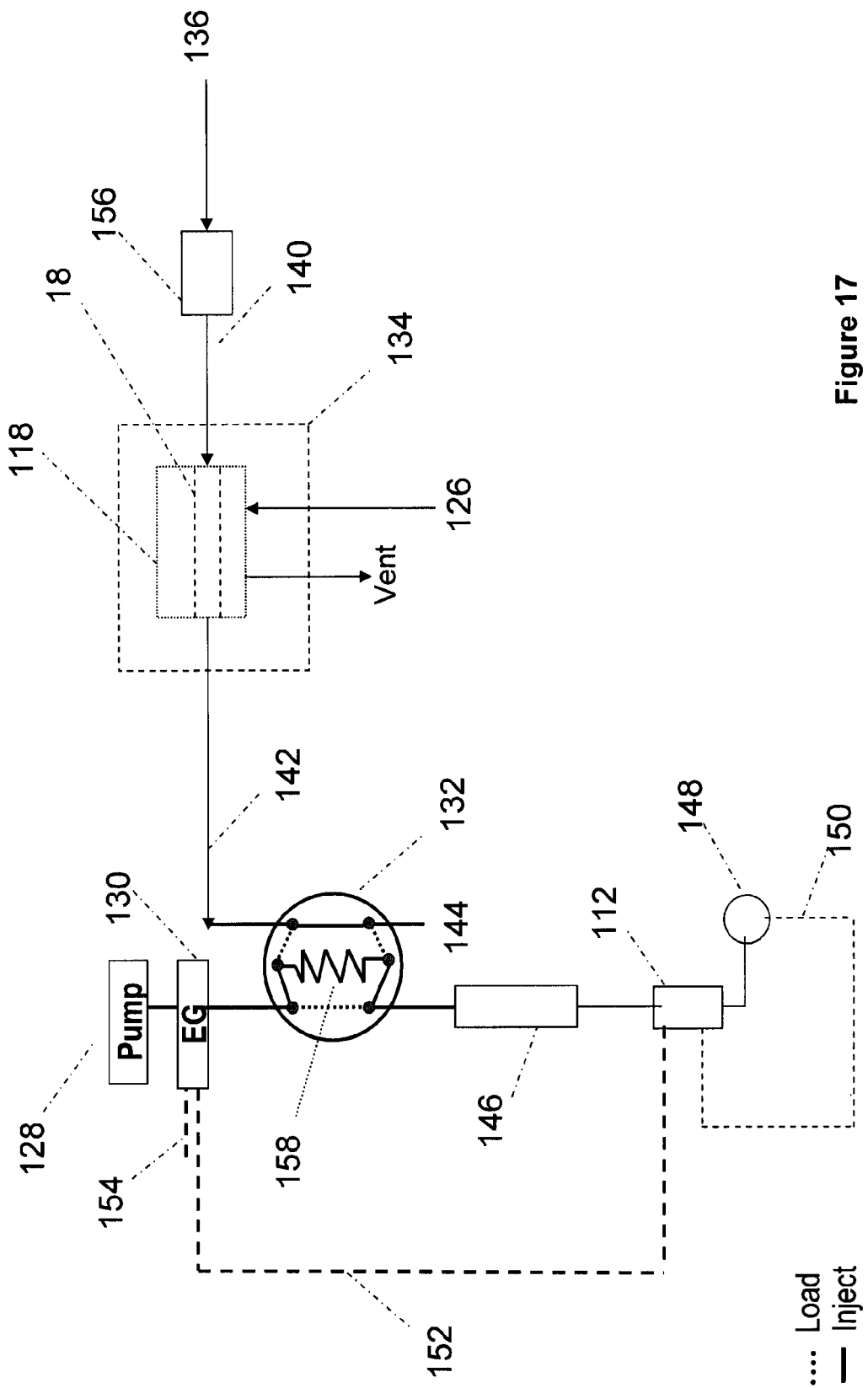

Another embodiment of the present invention is shown in FIG. 17. In operation and in instrumentation this embodiment is similar to Example 6 except a polisher column or suppressor 156 is used to remove any ions that would interact with the ion exchange membrane 18. For example during anion analysis the cations tend to interact with the cation exchange membrane and these cations can be removed using a cation polisher column 156 that has cation exchange material. It should be noted that the cation polisher column 156 could be replaced with a standard suppressor sold as ASRS or AMMS from Dionex Corporation. The cation polisher column 156 would have limited life time and would need to be replaced periodically or regenerated periodically. By removing the cations from the anion samples the membrane 18 is always in the hydronium form thereby maintaining the evaporation and concentrator function. For non ion exchange based hydrophilic membrane no such regeneration is needed.

Example 8

Figure 18:
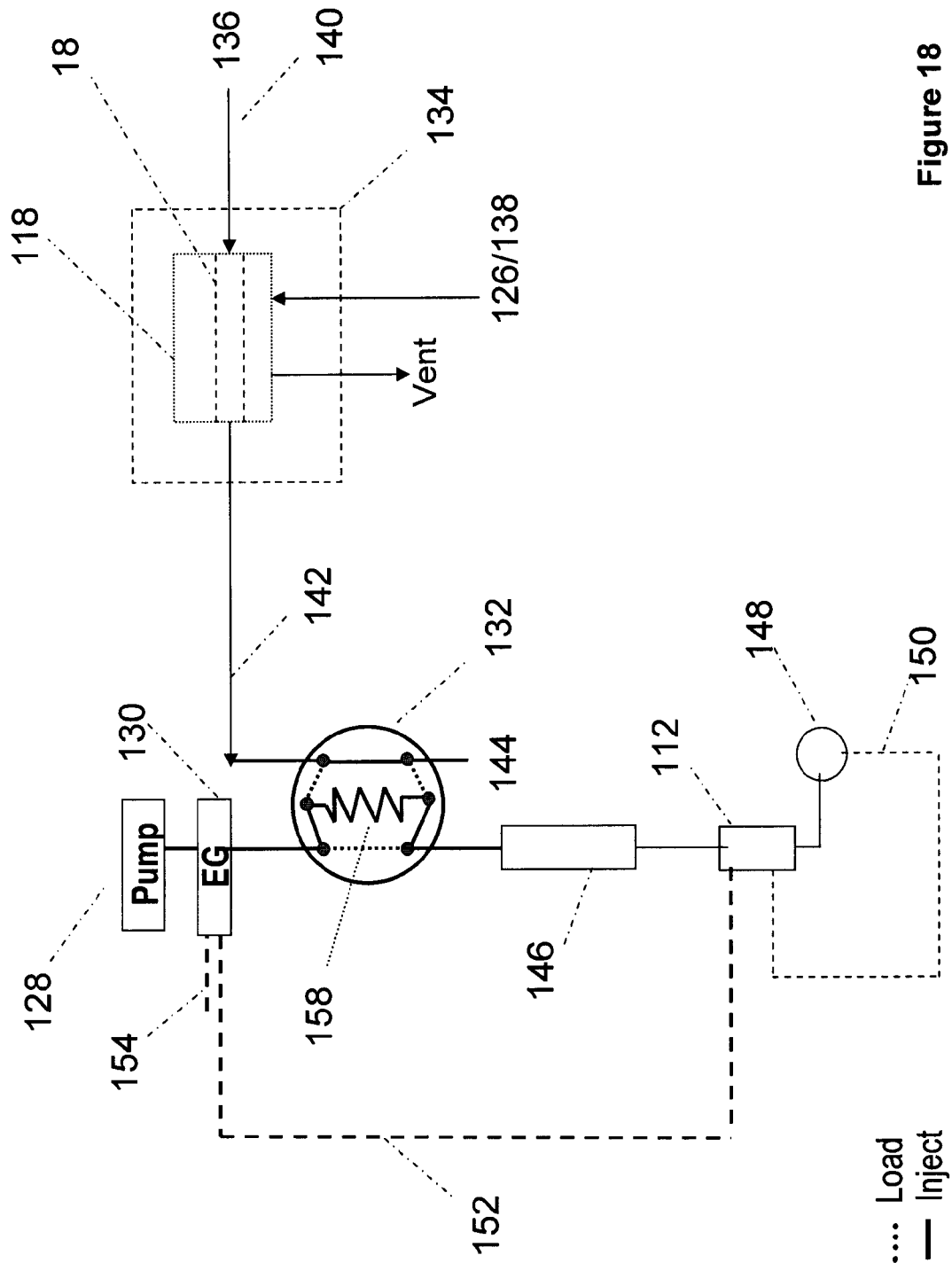

Another embodiment is shown in FIG. 18. This example most components are similar to example 6 except the regenerant 138 flows in a batch mode on the outside of the membrane 18 thereby regenerating the membrane. The gas stream has to be turned off during the regeneration step. The regeneration frequency depends on the sample as discussed in example 6. For non ion exchange based hydrophilic membrane no such regeneration is needed.

Example 9

Figure 19:
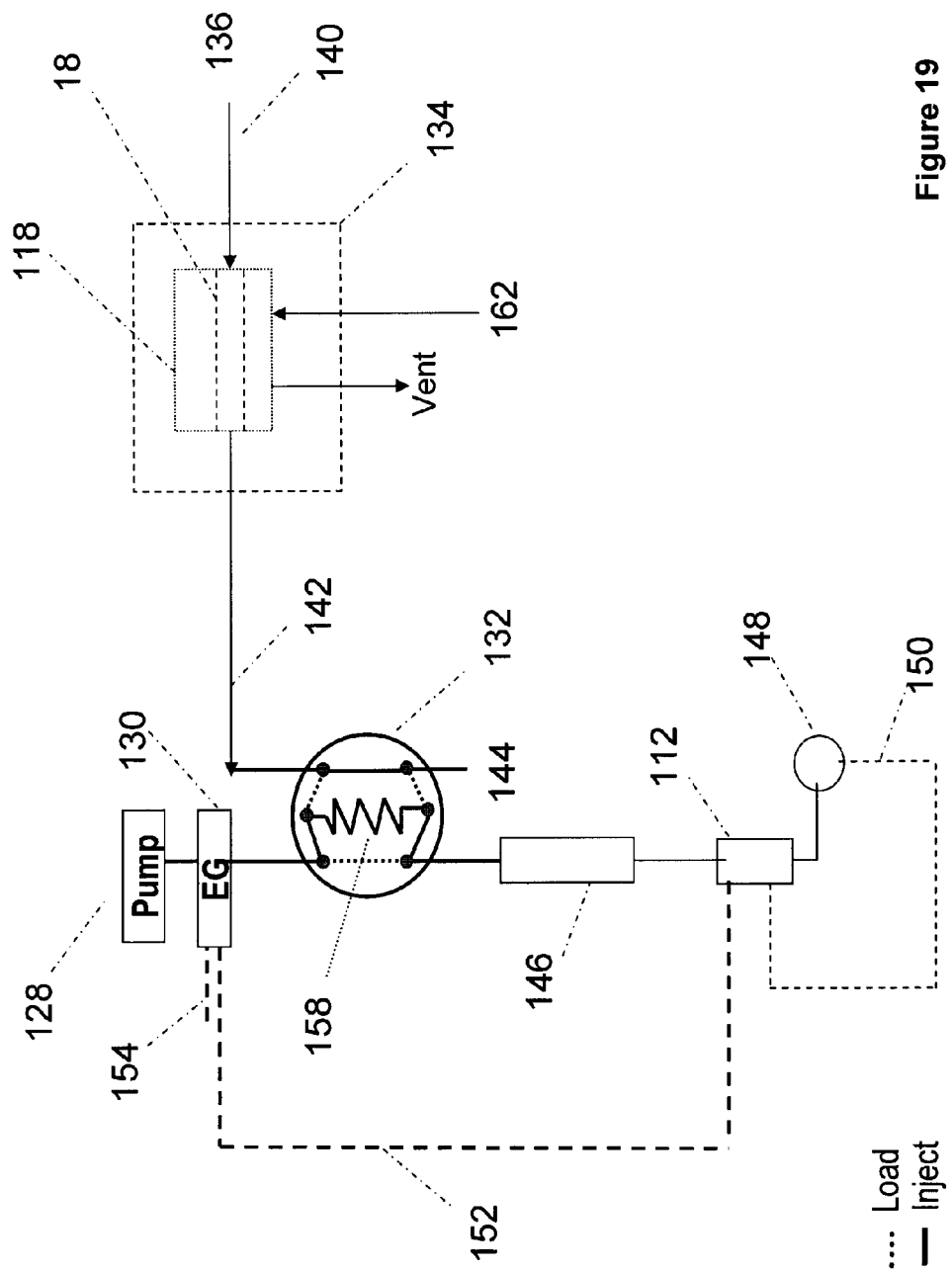

Another embodiment of the present invention is shown in FIG. 19. The setup and function is similar to example 8 except the gas stream is mixed with the regenerant and pumped into the evaporator device 118 for regenerating the membrane 18. The mixture of the gas and the regenerant does not have to be homogenous for the purpose of regenerating the membrane 18. For non ion exchange based hydrophilic membrane no such regeneration is needed.

Example 10

Figure 20:
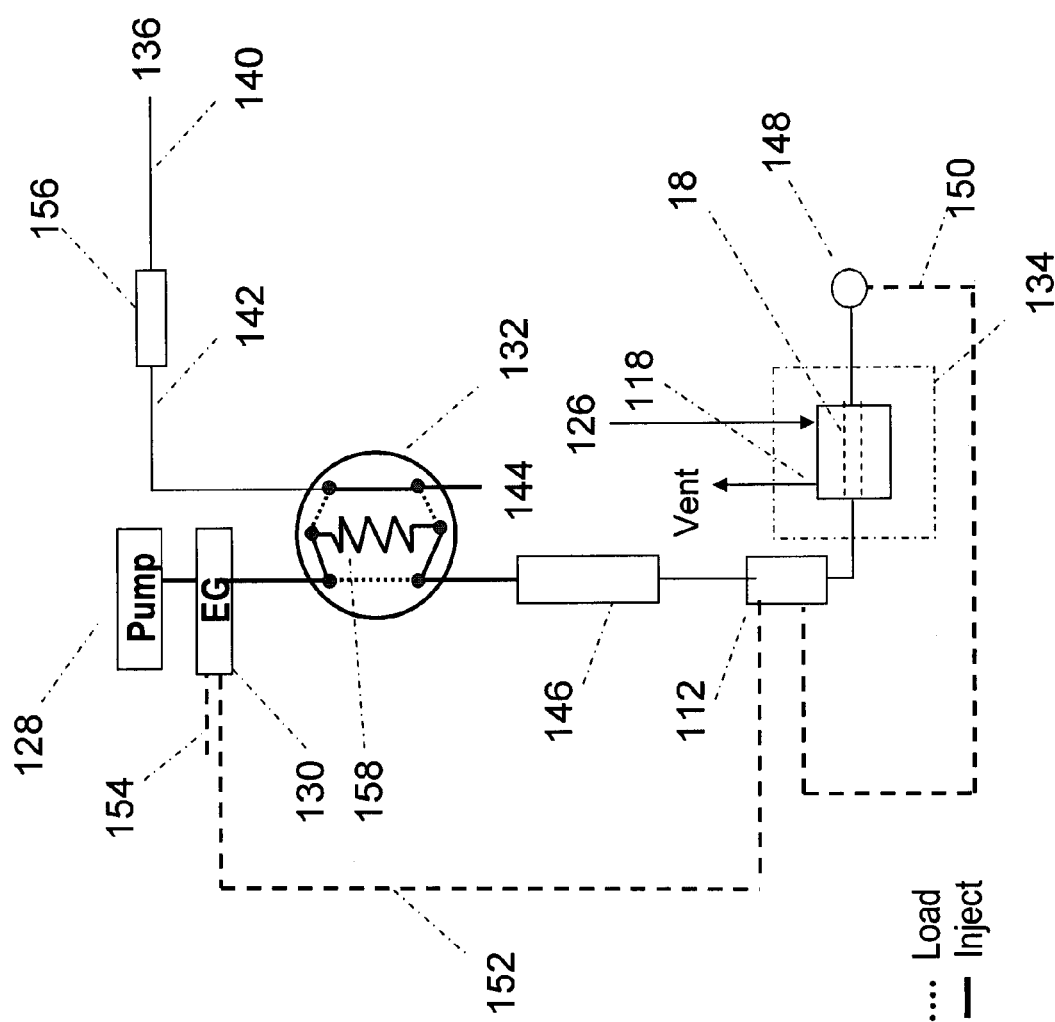

Another embodiment of the present invention is shown in FIG. 20. In this embodiment the membrane concentrator is used in the post separation setup. Referring to the figure, the sample 136 is pumped into a polisher column or suppressor 156 and then routed to the sample injection loop 158 via conduit 142 and then diverted to waste 144. The pump 128 is pumping DI water into an eluent generator module and the generated eluent is routed via an injection valve to column 146 where the sample components anions or cations are separated. The eluent is then routed through a suppressor to suppress the eluent and then routed through a membrane concentrator 118. The concentrated sample is detected in the detector cell 148. The cell effluent is routed via conduit 150 to the suppressor regenerant channel for regenerating the suppressor. The suppressor waste is routed via 152 to waste or back to the degas module (not shown) and then diverted to waste. In this embodiment when the membrane 18 is an ion exchange membrane the ions that interact with the ion exchange membrane 18 are removed prior to injection as per the present invention. When the membrane 18 is a non ion exchange hydrophilic membrane the column 156 is removed from this setup since the ions cannot react with this membrane.

Example 11

Figure 21:
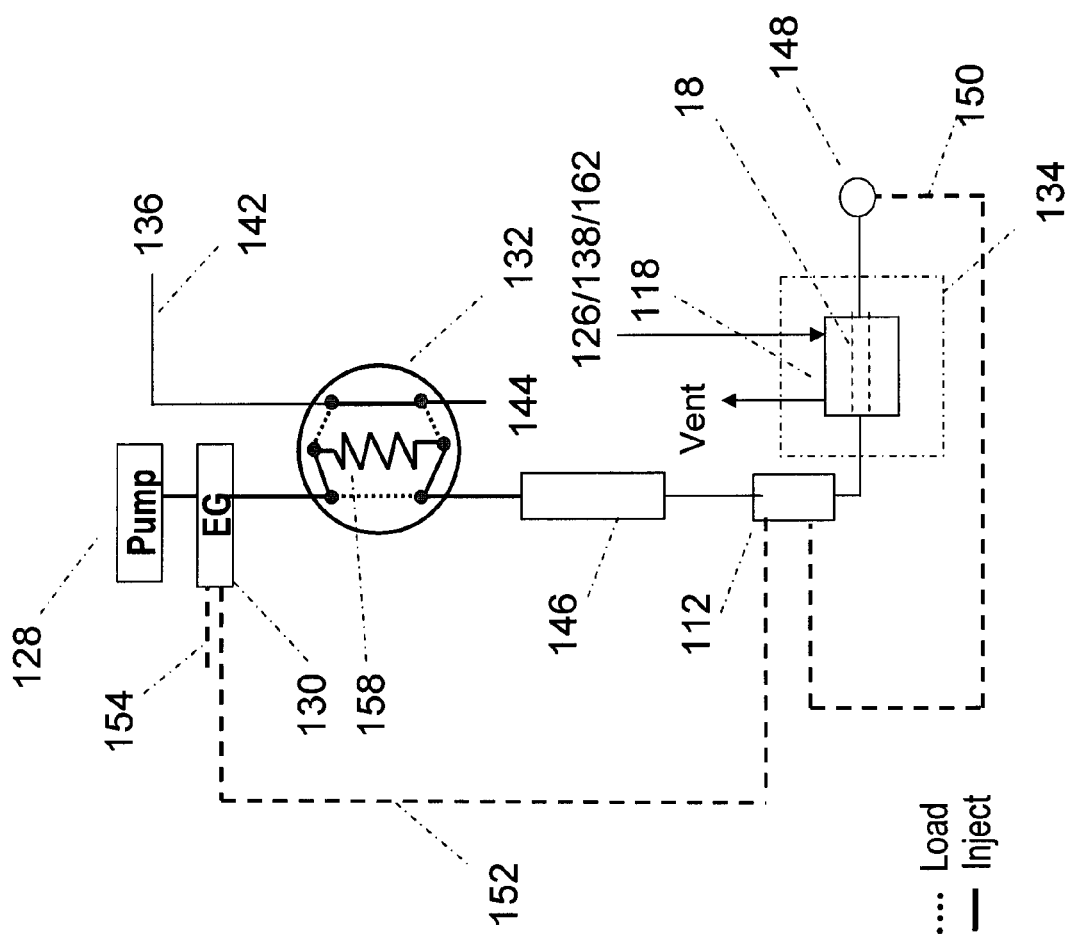

Another embodiment of the present invention is shown in FIG. 21. This embodiment is similar to the previously discussed example 10 except the sample is not treated for removing ions that interact with the membrane. A regeneration of the membrane 18 is invoked using a chemical regenerant as previously discussed. This regeneration can be accomplished in a batch mode by stopping the gas flow and then replacing the gas flow with regenerant flow. A mixture of gas and regenerant can also be used as discussed in example 9. For non ion exchange based hydrophilic membrane 18 no such regeneration is needed.

Example 12

Figure 22:
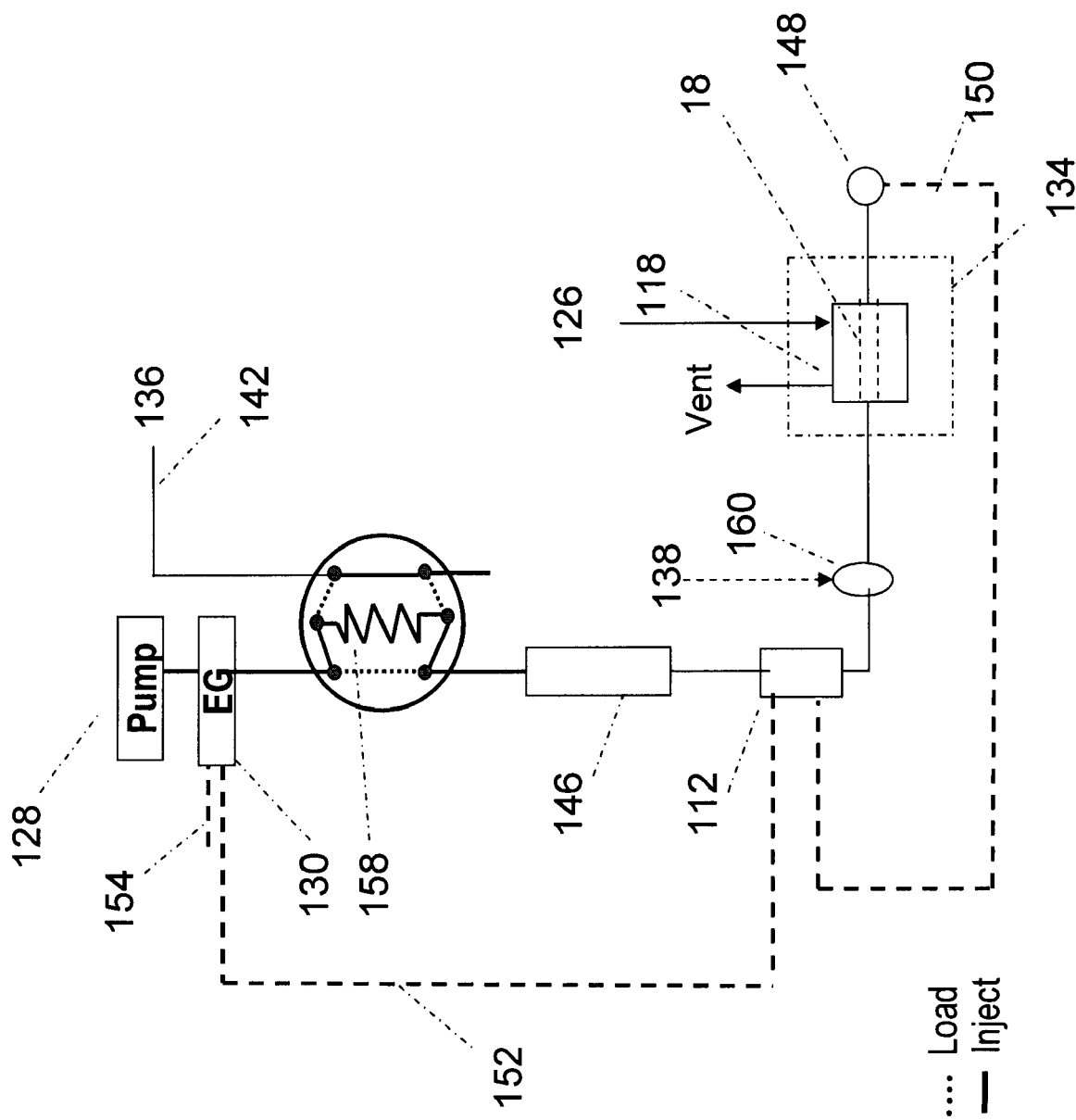

Yet another embodiment of the present invention is shown in FIG. 22. This example is similar to the previous example 11 except regeneration is achieved by pumping a regenerant stream 136 via a two way valve 160. In one position of the valve the valve allows the regeneration of the membrane 18 and in another position the valve stops the flow of regenerant to membrane concentrator 118. During the regeneration time the analysis has to cease and the flow from the suppressor is diverted to waste (not shown).

REFERENCES

1) Cappiello, A.; Famiglini, G.; Palma, P.; Siviero, A. *Mass Spectrom. Rev.* 2005, 24, 978-989.
2) Zwiener, C.; Frimmel, F. H. *Anal. Bioanal. Chem.* 2004, 378, 851-861.
3) Megoulas, N. C.; Koupparis, M. A. *Crit. Rev. Anal. Chem.* 2005, 35, 301-316.
4) Gormley P. G.; Kennedy, M. *Proc. Roy. Ir. Acad. Sci. Sect. A* 1949, 52, 163-169.
5) Ullah, S M. R.; Adams, R. L.; Srinivasan, K.; Dasgupta, P. K. *Anal. Chem.* 2004, 76, 7084-7093.
6) Dasgupta, P. K. *ACS Adv. Chem. Ser.* 1993, 232, 41-90.
7) Yeager, H. L. *ACS Symp. Ser.* 1982, 180, 49-64.
8) Waiz, S.; Cedillo, B. M.; Jambunathan, S.; Hohnholt, S. G.; Dasgupta, P. K.; Wolcott, D. K. *Anal. Chim. Acta* 2001, 428, 163-171.
9) Dasgupta, P. K. *Anal. Chem.* 1984, 56, 96-103.
10) Dasgupta, P. K. *Anal. Chem.* 1984, 56, 103-105.
11) Boring, C. B.; Al-Horr, R.; Genfa, Z.; Dasgupta, P. K. *Anal. Chem.* 2002, 74, 1256-1268.

What is claimed is:
1. A chromatography system including a sample concentrator for concentrating analytes in a solvent-containing liquid sample stream, said concentrator comprising
    (a) a concentrator housing having a sample stream flow channel and a gas stream flow channel having an inlet and an outlet,
    (b) a gas source,
    (c) a gas stream conduit providing continuous or discontinuous fluid communication between said gas source and said gas stream flow channel inlet,
    (d) a heater operatively associated with said gas source, gas stream conduit or gas stream flow channel,
    (e) a hydrophilic membrane barrier including ion exchange sites and separating said gas stream flow channel and said sample stream flow channel, said membrane barrier preventing bulk liquid flow but permitting the flow of solvent evaporated from said liquid sample stream in said sample stream flow channel in or at the interface with said membrane, when said gas stream is at an elevated temperature,
    (f) a source of a regenerant liquid in fluid communication with said gas stream flow channel or said sample stream flow channel, said chromatography system further comprising a chromatographic separator having an inlet and an outlet in fluid communication with said concentrator, said concentrator being downstream of said chromatographic separator outlet.

2. The apparatus of claim 1 in which said membrane is tubular.

3. The apparatus of claim 2 in which said membrane is a hollow fiber with an inner diameter between 1 and 1000 microns.

4. The apparatus of claim 1 in which said membrane is in the configuration of a sheet.

5. The apparatus of claim 1 further comprising a suppressor between the outlet of said chromatographic separator and the inlet of said concentrator sample stream flow channel and in fluidic communication therewith.

6. The apparatus of claim 5 in which said suppressor is a membrane suppressor comprising a suppressor membrane, said suppressor having a regenerant flow channel on the opposite side of said suppressor membrane separated from a liquid sample stream flow channel, said liquid sample stream flow channel being in fluid communication with said concentrator sample stream flow channel.

7. The apparatus of claim 2 in which said gas stream flow channel is an annular space defined by said tubular membrane and a coaxial external tube.

8. The apparatus of claim 1 in which said sample stream flow channel is in a serpentine configuration.

9. The apparatus of claim 1 in which said regenerant liquid is in fluid communication with said sample stream flow channel.

10. The apparatus of claim 7 further comprising valving operatively associated with said regenerant liquid source so that regenerant liquid flow can be blocked from flow into said sample stream flow channel when a sample liquid stream flows therethrough.

11. The apparatus of claim 1 in which said regenerant liquid is in fluid communication with said gas stream flow channel.

12. The apparatus of claim 1 further comprising a pair of electrodes on opposite sides of said membrane for electrolyzing water in said gas stream flow channel and sample stream flow channel.

13. A method of separating and concentrating analytes in a water-containing liquid sample stream, said method comprising
    (a) chromatographically separating said analytes in said water-containing liquid sample stream,
    (b) flowing the liquid sample stream from step (a) containing separated analytes at a first temperature through a sample stream flow channel in a sample concentrator separated from a gas stream flow channel by a hydrophilic membrane barrier including ion exchange sites,
    (c) concentrating the analytes by flowing a gas stream through said gas stream flow channel heated to a second temperature at least about 10° C. higher than the temperature of said liquid sample stream, to elevate the temperature of the liquid sample stream to cause a portion of the water in or at the interface with said membrane barrier to evaporate and flow through the membrane to be carried away in the flowing gas stream in said gas stream flow channel and (d) regenerating said ion exchange sites by flowing a regenerant solution through said gas stream flow channel or said sample stream flow channel.

14. The method of claim 13 in which said heating is performed intermittently.

15. The method of claim 13 in which the water evaporation rate is at least 20%.

* * * * *